US012588809B2

(12) United States Patent     (10) Patent No.:   US 12,588,809 B2

Hamrah et al.     (45) Date of Patent:    Mar. 31, 2026

(54) SYSTEMS AND METHODS FOR DETERMINING TISSUE INFLAMMATION LEVELS OF THE EYE FROM BLOOD VESSEL CHARACTERISTICS

(71) Applicant: Tufts Medical Center, Inc., Boston, MA (US)

(72) Inventors: Pedram Hamrah, Wellesley, MA (US); William Warr Binotti, Somerville, MA (US); Ricardo Menon Nose, Sao Paulo (BR)

(73) Assignee: Tufts Medical Center, Inc., Boston, MA (US)

( * ) Notice: Subject to any disclaimer, the term of this patent is extended or adjusted under 35 U.S.C. 154(b) by 412 days.

(21) Appl. No.: 18/140,195

(22) Filed: Apr. 27, 2023

(65) Prior Publication Data

US 2023/0263389 A1     Aug. 24, 2023

Related U.S. Application Data

(63) Continuation of application No. 17/766,892, filed as application No. PCT/US2020/054468 on Oct. 7, 2020, now Pat. No. 11,672,418.

(60) Provisional application No. 62/913,307, filed on Oct. 10, 2019.

(51) Int. Cl.
| | |
|---|---|
| *A61B 3/00* | (2006.01) |
| *A61B 3/10* | (2006.01) |
| *A61F 9/00* | (2006.01) |

(52) U.S. Cl.
CPC ............ *A61B 3/102* (2013.01); *A61F 9/0017* (2013.01)

(58) Field of Classification Search
CPC .............................. A61B 3/102; A61F 9/0017
See application file for complete search history.

(56) References Cited

U.S. PATENT DOCUMENTS

| | | |
|---|---|---|
| 6,293,674 B1 | 9/2001 | Huang et al. |
| 8,857,988 B2 | 10/2014 | Sharma et al. |
| 2013/0336557 A1 | 12/2013 | Cruzat et al. |
| (Continued) | | |

FOREIGN PATENT DOCUMENTS

| | | |
|---|---|---|
| JP | 2011-072446 A | 4/2011 |
| WO | 2019088555 A1 | 5/2019 |

OTHER PUBLICATIONS

Huang D et al. "Optical Coherence Tomography." Science. 1991; 254(5035): 1178-81.

(Continued)

*Primary Examiner* — Joel Lamprecht
*Assistant Examiner* — James F McDonald, III
(74) *Attorney, Agent, or Firm* — Young Basile Hanlon & MacFarlane, P.C.

(57) ABSTRACT

Disclosed are methods, systems, media, apparatus, devices, and other implementations, including a method that includes determining blood flow characteristics at an ocular surface of an eye of a patient, determining characteristics of blood vessels at the ocular surface of the eye based on the determined blood flow characteristics, and deriving one or more ocular redness grading scales indicative of inflammation levels of the eye of the patient based on the determined characteristics of the blood vessels at the ocular surface of the eye.

23 Claims, 18 Drawing Sheets

(56)                    References Cited

U.S. PATENT DOCUMENTS

| | | | | |
|---|---|---|---|---|
| 2014/0073917 A1* | 3/2014 | Huang | ................ | A61B 3/0025 |
| | | | | 600/427 |
| 2016/0058280 A1 | 3/2016 | Srivastava et al. | | |
| 2016/0228000 A1* | 8/2016 | Spaide | .................. | G06T 7/0012 |
| 2016/0287071 A1* | 10/2016 | Tan | ........................ | G06T 7/0012 |
| 2016/0317026 A1 | 11/2016 | Fingler et al. | | |
| 2016/0331229 A1 | 11/2016 | Huang et al. | | |
| 2018/0182082 A1 | 6/2018 | Jia et al. | | |

OTHER PUBLICATIONS

Watson, P, and A Romano. "The impact of new methods of investigation and treatment on the understanding of the pathology of scleral inflammation." Eye (London, England) vol. 28,8 (2014): 915-30. doi:10.1038/eye.2014.110.

Read, S., Alonso-Caneiro, D., Vincent, S. et al. "Anterior eye tissue morphology: Scleral and conjunctival thickness in children and young adults." Sci Rep 6, 33796 (2016). https://doi.org/10.1038/srep33796.

Gao, Simon S et al. "Optical Coherence Tomography Angiography." Investigative Ophthalmology & Visual Science vol. 57,9 (2016): OCT27-36. doi:10.1167/iovs.15-19043.

Ang M, Cai Y, Shahipasand S, et al "En face optical coherence tomography angiography for corneal neovascularisation" British Journal of Ophthalmology 2016; 100:616-621.

Anijeet, Deepa Rajeswari et al. Imaging and evaluation of corneal vascularization using fluorescein and indocyanine green angiography. Investigative ophthalmology & visual science 53 2 (2012): 650-8 . DOI:10.1167/iovs.11-8014.

Santosh G. K. Gadde et al. "Quantification of Vessel Density in Retinal Optical Coherence Tomography Angiography Images Using Local Fractal Dimension." Invest. Ophthalmol. Vis. Sci. 2016;57(1):246-252. doi: https://doi.org/10.1167/iovs.15-18287.

Adeleh Yarmohammadi et al. "Optical Coherence Tomography Angiography Vessel Density in Healthy, Glaucoma Suspect, and Glaucoma Eyes." Invest. Ophthalmol. Vis. Sci. 2016;57(9):OCT451-OCT459. doi: https://doi.org/10.1167/iovs.15-18944.

Galina Dimitrova et al. "Quantitative Retinal Optical Coherence Tomography Angiography in Patients With Diabetes Without Diabetic Retinopathy." Invest. Ophthalmol. Vis. Sci. 2017;58(1):190-196. doi: https://doi.org/10.1167/iovs.16-20531.

* cited by examiner

AS-OCTA Case

VD= 60.3%

520

510

AS-OCTA Control

VD= 54.6%

Correlations

562

| Redness | | Temporal | Nasal | Total |
|---|---|---|---|---|
| Redness | Pearson Correlation | .670** | .610* | .760** |
| | Sig. (2-tailed) | .001 | .027 | .000 |

**. Correlation is significant at the 0.01 level (2-tailed).

*. Correlation is significant at the 0.05 level (2-tailed).

FIG. 5D

*Table 1*

600

| Parameters | Controls | CLW | DED | AOI | p-value |
|---|---|---|---|---|---|
| Age (years) | 35.6±14.4 | 28.6±2.8 | 56.6±20.0 | 38.8±11.8 | <0.001*** |
| N Males (Total N) | 6(7) | 3(6) | 0(5) | 4(4) | <0.001*** |
| Mean Vessel Cutoff Depth (μm) | 193.9±7.9 | 191.5±6.7 | 179.5±7.1 | 181.6±7.8 | <0.001*** |
| Mean Conjunctival Thickness (μm) | 236.3±11.0 | 242.0±7.3 | 250.4±6.5 | 263.2±14.0 | <0.001*** |
| Percentage of Superficial Vessels In Conjunctiva (%) | 81.9±5.0 | 79.2±3.4 | 71.7±2.8 | 70.0±5.8 | <0.001*** |

Full Thickness

| Parameters | Controls | CLW | DED | AOI | p-value |
|---|---|---|---|---|---|
| VD (%) | 31.1±2.5 | 34.2±2.3 | 34.8±3.7 | 39.8±6.2 | <0.001*** |
| VDI | 2.89±0.16 | 3.05±0.09 | 2.98±0.25 | 3.17±0.24 | <0.002** |
| FD | 1.624±0.026 | 1.636±0.016 | 1.630±0.020 | 1.647±0.006 | <0.008** |

Superficial Plexus

| Parameters | Controls | CLW | DED | AOI | p-value |
|---|---|---|---|---|---|
| VD (%) | 27.3±2.8 | 30.4±2.3 | 31.1±2.9 | 31.8±4.4 | <0.001*** |
| VDI | 2.78±0.20 | 2.98±0.11 | 2.97±0.18 | 3.04±0.25 | 0.001*** |
| FD | 1.601±0.030 | 1.605±0.015 | 1.590±0.026 | 1.592±0.020 | 0.824 |

Deep Plexus

| Parameters | Controls | CLW | DED | AOI | p-value |
|---|---|---|---|---|---|
| VD (%) | 29.1±3.1 | 32.4±2.6 | 33.0±3.8 | 38.9±7.1 | <0.001*** |
| VDI | 2.88±0.13 | 2.99±0.09 | 3.04±0.20 | 3.18±0.25 | 0.005** |
| FD | 1.610±0.031 | 1.627±0.017 | 1.615±0.017 | 1.640±0.013 | 0.014* |
| Total Eyes | 11 | 12 | 9 | 7 | |

FIG. 6A

_Table 2_

610

| | | TOTAL | p-value | CTRL | p-value | CLW | p-value | DED | p-value | AOI | p-value |
|---|---|---|---|---|---|---|---|---|---|---|---|
| VD (%) | Temporal | 34.4±4.5 | 0.452 | 31.6±3.4 | 0.632 | 35.02±3.02 | 0.055 | 34.57±3.97 | 0.893 | 37.98±6.93 | 0.005** |
| | Nasal | 39.9±4.7 | | 30.7±2.7 | 0.632 | 33.48±2.31 | | 33.36±2.87 | | 40.35±6.39 | |
| VDI | Temporal | 3.00±0.22 | 0.11 | 2.91±0.20 | 0.690 | 3.05±0.11 | 0.581 | 2.96±0.32 | 0.219 | 3.09±0.26 | 0.082 |
| | Nasal | 3.04±0.18 | | 2.93±0.14 | 0.690 | 3.06±0.10 | | 2.99±0.2 | | 3.2±0.26 | |
| FD | Temporal | 1.639±0.025 | 0.062 | 1.629±0.029 | 0.807 | 1.643±0.023 | 0.066 | 1.636±0.027 | 0.392 | 1.651±0.017 | 0.537 |
| | Nasal | 1.629±0.022 | | 1.616±0.029 | | 1.629±0.017 | | 1.634±0.016 | | 1.644±0.012 | |

SYSTEMS AND METHODS FOR DETERMINING TISSUE INFLAMMATION LEVELS OF THE EYE FROM BLOOD VESSEL CHARACTERISTICS

CROSS-REFERENCE TO RELATED APPLICATIONS

This application is a continuation of U.S. application Ser. No. 17/766,892, filed Apr. 6, 2022, which is a national stage entry under 35 U.S.C. 371 of International Application No. PCT/US2020/054468, filed Oct. 7, 2022, which claims the benefit of the filing date of U.S. Provisional Application No. 62/913,307, filed Oct. 10, 2019, the contents of all of which are herein incorporated by reference in their entireties.

BACKGROUND

Ocular redness is a consequence of ocular surface irritation and inflammation, often correlating to ocular symptoms and severity. The conjunctival vasculature is known to play an important role in ocular surface diseases, which dilate and become tortuous in response to inflammatory stimulus, resulting in the redness appearance. Ocular surface disease is a term that involves many diseases, such as inflammatory diseases, (i.e. ocular allergies, dry eye disease, and inflammatory anterior uveitis) and infectious diseases (i.e. viral, bacterial, fungal or parasitic) that affect the ocular surface, at least in part.

Practitioners most commonly resort to illustrative grading scales for the monitoring of their patients; these commonly available scales are produced using either photographic images or images which have been artistically rendered and normally range from 0-4 (no conjunctival redness or normal to severe conjunctival redness). These allow clinicians to classify an ocular condition according to referenced levels of severity depicted by the images of the scale. There is a wide range of ocular redness grading scales used to assess the severity of ocular symptoms. The majority of such scales rely on subjective parameters with wide variability and little consistency between practitioners.

SUMMARY

Disclosed are systems, apparatus, devices, circuits, methods, and other implementations that use optical coherence tomography (OCT) imaging approaches to determine blood vessel characteristics at a patient's ocular surface (e.g., determine blood flow extent and behavior at the ocular surface, which is representative of vasculature mapping at the ocular surface). Determined blood vessel characteristics of the ocular surface is in turn indicative of inflammation levels of the patient's eye (e.g., higher vessel density and diameter indicates higher inflammation levels).

More particularly, embodiments described herein implement anterior segment (AS) optical coherence tomography angiography (OCTA) imaging approaches to non-invasively evaluate conjunctival vessels through-flow, based on which an objective and quantitative way of assessing ocular redness, and thus ocular inflammation levels, is provided (that can supplement or supplant subjective clinical grading). It is known that conjunctival vessel morphology changes in response to ocular inflammation, and therefore an objective methodology as the ones disclosed herein can improve ocular surface diseases assessment and its response to treatment. AS-OCTA parameters of vessel morphology and density (and/or a metric derived based on those parameters) can be used to quantify ocular surface inflammation. The approaches described herein can improve classification, grading and monitoring of patients with ocular surface diseases, and provide reliable, reproducible and objective assessments as a robust element in clinical practice. The implementations described herein can further be translated for use in improvement/establishment of diagnosis, relate signs to diagnosis, assess prognosis and response to therapy in the above-mentioned diseases treatment, and can also be useful for clinical trials.

In some embodiments, determination of ocular redness may also be based on in vivo confocal microscopy. The ocular surface comprises the conjunctiva, which is a semi-transparent membrane that covers the sclera, and the cornea, an avascular and transparent ocular tissue. There is a close interaction between these neighboring structures, where cells can migrate in an inflammatory response. These inflammatory cells are responsible for altering the vasculature characteristics of the conjunctiva and limbus (area of transition between cornea and sclera/conjunctiva). In vivo confocal microscopy is a laser scanning imaging tool, which enables visualization of the cornea and conjunctiva at a cellular level, including dendritic cells.

In some variations, a method is provided that includes determining blood flow characteristics at an ocular surface of an eye of a patient, determining characteristics of blood vessels at the ocular surface of the eye based on the determined blood flow characteristics, and deriving one or more ocular redness grading scales indicative of inflammation levels of the eye of the patient based on the determined characteristics of the blood vessels at the ocular surface of the eye.

Embodiments of the method may include at least some of the features described in the present disclosure, including one or more of the following features.

Determining the blood flow characteristics at the ocular surface of the eye may include performing anterior segment (AS) optical coherence tomography angiography (OCTA) imaging for the ocular surface to detect blood flow at the ocular surface of the eye.

Performing AS-OCTA for the ocular surface may include producing images, based on the detected blood flow, representing a vasculature distribution at the ocular surface of the eye.

Performing AS-OCTA for the ocular surface to detect blood flow at the ocular surface of the eye may include obtaining blood flow image data for multiple layers of the ocular surface, the multiple layers including one or more of, for example, cornea, limbus, conjunctiva, episcleral, and/or sclera.

Obtaining the blood flow image data the multiple layers may further include dividing the image data for at least one of the multiple layers, based on a respective reference depth for the at least one of the multiple layers, into one or more of, for example, a superficial layer image data, deep layer image data, and/or full thickness image data.

The method may further include separating the blood flow image data into separate blood flow image data sets for one or more of the multiple layers.

Separating the blood flow image data into separate blood flow image data sets for the respective multiple layers may include separating the blood flow image data into the separate blood flow image data sets using machine learning techniques.

Performing AS-OCTA imaging for the ocular surface may include controllably adjusting focus of a lens assembly of an OCT imaging apparatus based on one or more of, for example, controllably actuating a focus-motor of the OCT imaging apparatus, and/or controllably actuating a z-motor of the OCT imaging apparatus to control the distance between the lens assembly and the eye of the patient.

Performing AS-OCTA imaging for the ocular surface may include controlling an optical emission source of an OCT imaging apparatus to provide optical radiation controllably directed at the ocular surface, including performing one or more of, for example, controllably adjusting the optical radiation directed to the eye of the patient so that light reflectance behavior is affected by tissue at the ocular surface of the eye, and/or controllably actuating activation and de-activation of the optical emission source provided to the OCT imaging apparatus.

Determining characteristics of the blood vessels at the ocular surface of the eye may include determining one or more of, for example, vessel density of the blood vessels at the ocular surface, diameters attributes of at least some of the blood vessels, and/or vasculature branching pattern attributes for the blood vessels measured by fractal dimension.

Determining the characteristics of the blood vessels at the ocular surface may include obtaining one or more images representative of a vasculature mapping at the ocular surface of the eye based on the determined blood flow characteristics, and processing the one or more images to determine the characteristics of the blood vessels based on image data from the processed one or more images.

Processing the one or more images may include identifying pixels, for a particular image from the one or more images, representing blood vessels in the image, determining a ratio of the identified pixels representing the blood vessels in the image and total number of pixels in the particular image, and determining the vessel density based on the determined ratio.

Identifying the pixels may include binarizing the particular image to convert pixels value into either a pre-determined pixel value representing blood flow, or another pre-determine pixel value representing no blood flow.

Processing the one or more images may include identifying pixels, for a particular image from the one or more images, representing non-vessel objects in the particular image, generating a skeletonized image corresponding to the particular image comprising skeleton representations of blood vessels appearing in the particular image, identifying skeletonized pixels, for the skeletonized image, representing non-vessel objects in the skeletonized image, and deriving a vessel diameter index based on the identified pixels representing the non-vessel objects in the particular image and the identified skeletonized pixels representing the non-vessel objects in the skeletonized image.

Processing the one or more images may include performing fractal dimension analysis of vessels appearing in the one or more images to determine vasculature branching pattern complexity of the blood vessels at the ocular surface of the eye.

The method may further include determining one or more medical conditions of the patient based on the derived one or more ocular redness measures.

In some variations, a system to determine inflammation level of an eye of a patient is provided. The system includes an imaging apparatus to determine blood flow characteristics at an ocular surface of the eye of the patient, and a controller configured to determine characteristics of blood vessels at the ocular surface of the eye based on the determined blood flow characteristics, and derive one or more ocular redness grading scales indicative of inflammation levels of the eye of the patient based on the determined characteristics of the blood vessels at the ocular surface of the eye.

Embodiments of the system may include at least some of the features described in the present disclosure, including at least some of the features described above in relation to the method, as well as one or more of the following features.

The imaging apparatus may include an anterior segment (AS) optical coherence tomography angiography (OCTA) imaging apparatus. The controller configured to determine the blood flow characteristics at the ocular surface of the eye may be configured to perform AS-OCTA imaging for the ocular surface to detect blood flow at the ocular surface of the eye.

The AS-OCTA imaging apparatus may be configured to produce images based on the detected blood flow representing a vasculature distribution at the ocular surface of the eye.

The controller configured to perform AS-OCTA imaging for the ocular surface to detect blood flow at the ocular surface may be configured to obtain blood flow image data for multiple layers of the ocular surface, with the multiple layers including one or more of, for example, cornea, limbus, conjunctiva, episcleral, and/or sclera. The controller may also be configured to separate the blood flow image data into separate blood flow image data sets for one or more of, for example, respective multiple layers, or into one or more of, for example, a superficial layer, a deep layer, and/or full thickness layer.

The controller may further include a machine learning engine configured to separate the blood flow image data into the separate blood flow image data sets based on machine learning techniques.

The controller to perform AS-OCTA imaging for the ocular surface may be configured to controllably adjust focus of a lens assembly coupled to an OCT imaging apparatus based on one or more of, for example, controllably actuating a focus-motor of the OCT imaging apparatus, and/or controllably actuating a z-motor of the OCT imaging apparatus to control the distance between the lens assembly and the eye of the patient.

The controller to perform AS-OCTA for the ocular surface may be configured to controllably actuate activation and de-activation of the optical emission source provided to the OCT imaging apparatus.

The controller configured to determine characteristics of the blood vessels at the ocular surface of the eye may be configured to determine one or more of, for example, vessel density of the blood vessels at the ocular surface, diameter attributes of at least some of the blood vessels, and/or vasculature branching pattern attributes for the blood vessels measured by fractal dimension.

The controller configured to determine the characteristics of the blood vessels at the ocular surface may be configured to obtain one or more images representative of a vasculature mapping at the ocular surface of the eye based on the determined blood flow characteristics, and process the one or more images to determine the characteristics of the blood vessels based on image data from the processed one or more images.

The controller configured to process the one or more images may be configured to identify pixels, for a particular image from the one or more images, representing blood vessels in the image, determine a ratio of the identified pixels representing the blood vessels in the image and total number of pixels in the particular image, and determine the vessel density based on the determined ratio.

The controller configured to process the one or more images may be configured to identify pixels, for a particular image from the one or more images, representing non-vessel objects in the particular image, generate a skeletonized image comprising skeleton representations of blood vessels appearing in the particular image, identify skeletonized pixels, for the skeletonized image, representing non-vessel objects in the skeletonized image, and derive a vessel diameter index based on the identified pixels representing the non-vessel objects in the particular image and the identified skeletonized pixels representing the non-vessel objects in the skeletonized image.

The controller configured to process the one or more images may be configured to perform fractal dimension analysis of vessels appearing in the one or more images to determine vasculature branching pattern complexity of the blood vessels at the ocular surface of the eye.

In some variations, a non-transitory computer readable media is provided, that includes computer instructions, executable on one or more processor-based devices, to determine blood flow characteristics at an ocular surface of an eye of a patient, determine characteristics of blood vessels at the ocular surface of the eye based on the determined blood flow characteristics, and derive one or more ocular redness grading scales indicative of inflammation levels of the eye of the patient based on the determined characteristics of the blood vessels at the ocular surface of the eye.

Embodiments of the computer readable media may include at least some of the features described in the present disclosure, including at least some of the features described above in relation to the method and the system.

In some variations, a method for therapeutic monitoring is provided. The method includes obtaining, at a first time instance, a first set of data representing a first ocular grading scale, including determining first blood flow characteristics at an ocular surface of an eye of a patient, determining first characteristics of blood vessels at the ocular surface of the eye based on the determined first blood flow characteristics, and deriving the first ocular grading scale based on the determined first characteristics of the blood vessels at the ocular surface of the eye. The method further includes obtaining, at a second time instance, a second set of data representing a second ocular grading scale, including determining second blood flow characteristics at the ocular surface of the eye of the patient, determining second characteristics of blood vessels at the ocular surface of the eye based on the determined second blood flow characteristics, and deriving the second ocular grading scale based on the determined second characteristics of the blood vessels at the ocular surface of the eye. The method additionally includes determining at least one parameter representing a change between the first set of data and the second set of data.

Embodiments of the therapeutic monitoring method may include at least some of the features described in the present disclosure, including at least some of the features described above in relation to the first method, the system, and the computer readable media, as well as one or more of the following features.

The method may further include providing an output indicative of the at least one parameter representing the change between the first set of data and the second set of data.

Determining the at least one parameter representing the change between the first set of data and the second set of data may include computing a percentage change between the second ocular grading scale and the first ocular grading scale.

The method may further include administering to the patient a selected therapeutic medication following the obtaining of the first set of data such that the second blood vessel characteristics are determined in response to the selected therapeutic medication administered to the patient.

The determined at least one parameter representing the change between the first set of data and the second set of data may be representative, at least in part, of an effect of the selected therapeutic medication on changes to ocular redness level in the eye of the patient.

The method may further include determining efficacy of the selected therapeutic medication, or an existence of an adverse event (AE) or a serious adverse event (SAE), based on the determined at least one parameter representing the change between the first set of data and the second set of data after administering the selected therapeutic medication.

Administering to the patient the selected therapeutic medication may include administering to the patient one or more of, for example, an anti-inflammatory steroid and/or an immunosuppressive agent.

The method may further include selecting the patient from a pool of candidate subjects available to test efficacy of the selected therapeutic medication. Selecting the patient may include determining, subsequent to obtaining the first set of data, that the patient potentially suffers from a particular medical condition based on a comparison of the first ocular grading scale derived for the patient to a reference value. Another candidate subject from the pool may be excluded from receiving the selected therapeutic medication in response to a determination, based on another comparison of a respective other first ocular grading scale derived for the other candidate to the reference value, that the other candidate subject likely does not suffer from the particular medical condition.

The method may further include determining one or more of a medical condition and/or a severity of the medical condition, of the patient, based, at least in part, on at least the first ocular grading scale.

The method may further include determining a medication with an associated dosage for treating the medical condition or the severity of the medical condition, and administering the medication at the associated dosage.

The method may further include subsequent to administering the medication at the associated dosage, determining whether to adjust one or more of the medication or the associated dosage for the medication based on the at least one parameter representing the change between the first set of data and the second set of data.

The method may further include determining at subsequent time instances, subsequent to administering the medication at the associated dosage, based on subsequently obtained sets of data, a level of responsiveness of the patient to the medication at the associated dosage, with the subsequent time instances including at least the second time instance, and with the subsequent sets of data including at least the second set of data.

The method may further include providing an output indicative of the level of responsiveness of the patient to the medication at the associated dosage.

Obtaining the first set of data and obtaining the second set of data may further include determining at the first time instance and at the second time instance one or more of, for example, (i) density of dendritic immune cells present in a cornea of the eye of the patient, (ii) average size of the dendritic immune cells present in the cornea of the eye of the patient, (iii) average area covered by the dendritic immune cells present in the cornea of the eye of the patient, (iv)

number or average density of dendritic inflammatory cells present in a peripheral cornea of the eye of the patient, (v) a hyperreflectivity of epithelial cells in a conjunctiva of the eye of the patient, (vi) dendritic cell density in the conjunctiva of the eye of the patient, (vii) average dendritic cell size in the conjunctiva of the eye of the patient, (viii) number of hyperreflective dendritic cells in the conjunctiva of the eye of the patient, (ix) dilation of lumen of blood vessels in the conjunctiva of the eye of the patient, (x) average size of inflammatory cells in the blood vessels in the conjunctiva of the eye of the patient, (xi) a sticking value, representative of an average time of transitory residence of inflammatory cells to the blood vessels walls in the conjunctiva of the eye of the patient, (xii) average size of inflammatory cells in the lymph vessels in the conjunctiva of the eye of the patient, and/or (xiii) a number of inflammatory cells present in the lymph vessels of the conjunctiva of the eye of the patient.

Determining the at least one parameter representing the change between the first set of data and the second set of data may further include determining level of change between the first time instance and the second time instance of one or more of, for example, (i) a change in the density of dendritic immune cells present in a cornea of the eye of the patient, (ii) a change in the average size of the dendritic immune cells present in the cornea of the eye of the patient, (iii) a change in the average area covered by the dendritic immune cells present in the cornea of the eye of the patient, (iv) a change in the number or average density of dendritic inflammatory cells present in a peripheral cornea of the eye of the patient, (v) a change in the hyperreflectivity of epithelial cells in a conjunctiva of the eye of the patient, (vi) a change in the dendritic cell density in the conjunctiva of the eye of the patient, (vii) a change in the average dendritic cell size in the conjunctiva of the eye of the patient, (viii) a change in the number of hyperreflective dendritic cells in the conjunctiva of the eye of the patient, (ix) a change in dilation of lumen of blood vessels in the conjunctiva of the eye of the patient, (x) a change in the average size of inflammatory cells in the blood vessels in the conjunctiva of the eye of the patient, (xi) a change in the sticking value, representative of the average time of transitory residence of inflammatory cells to the blood vessels walls in the conjunctiva of the eye of the patient, (xii) a change in the average size of inflammatory cells in the lymph vessels in the conjunctiva of the eye of the patient, and/or (xiii) a change in the number of inflammatory cells present in the lymph vessels of the conjunctiva of the eye of the patient.

Determining the first blood flow characteristics and the second blood flow characteristics at the ocular surface of the eye of the patient may include performing at the first time instance and at the second time instance anterior segment (AS) optical coherence tomography angiography (OCTA) imaging for the ocular surface to detect blood flow at the ocular surface of the eye, and to produce images, based on the detected blood flow, representing a vasculature distribution at the ocular surface of the eye.

Performing AS-OCTA for the ocular surface to detect blood flow at the ocular surface of the eye may include obtaining blood flow image data for multiple layers of the ocular surface, the multiple layers including one or more of, for example, cornea, limbus, conjunctiva, episcleral, and/or sclera.

Obtaining the blood flow image data the multiple layers may further include dividing the image data for at least one of the multiple layers, based on a respective reference depth for the at least one of the multiple layers, into one or more of, for example, a superficial layer image data, deep layer image data, and/or full thickness image data.

The method may further include separating the blood flow image data into separate blood flow image data sets for one or more of the multiple layers.

In some variations, a therapeutic monitoring system is provided that includes an imaging apparatus to determine blood flow characteristics at an ocular surface of the eye of the patient, and a controller. The controller is configured to obtain, at a first time instance, a first set of data representing a first ocular grading scale, including to determine first blood flow characteristics at an ocular surface of an eye of a patient, determine first characteristics of blood vessels at the ocular surface of the eye based on the determined first blood flow characteristics, and derive the first ocular grading scale based on the determined first characteristics of the blood vessels at the ocular surface of the eye. The controller is additionally configured to obtain, at a second time instance, a second set of data representing a second ocular grading scale, including to determine second blood flow characteristics at the ocular surface of the eye of the patient, determine second characteristics of blood vessels at the ocular surface of the eye based on the determined second blood flow characteristics, and derive the second ocular grading scale based on the determined second characteristics of the blood vessels at the ocular surface of the eye. The controller is also configured to determine at least one parameter representing a change between the first set of data and the second set of data.

In some variations, an additional non-transitory computer readable media is provided, that includes computer instructions, executable on one or more processor-based devices, to obtain, at a first time instance, a first set of data representing a first ocular grading scale, including to determine first blood flow characteristics at an ocular surface of an eye of a patient, determine first characteristics of blood vessels at the ocular surface of the eye based on the determined first blood flow characteristics, and derive the first ocular grading scale based on the determined first characteristics of the blood vessels at the ocular surface of the eye. The computer instructions further cause the one or more processor-based devices to obtain, at a second time instance, a second set of data representing a second ocular grading scale, including to determine second blood flow characteristics at the ocular surface of the eye of the patient, determine second characteristics of blood vessels at the ocular surface of the eye based on the determined second blood flow characteristics, and derive the second ocular grading scale based on the determined second characteristics of the blood vessels at the ocular surface of the eye. And the computer instructions additionally cause the one or more processor-based devices to determine at least one parameter representing a change between the first set of data and the second set of data.

Embodiments of the therapeutic monitoring system and the additional computer readable media may include at least some of the features described in the present disclosure, including at least some of the features described above in relation to the methods, the first system, and the first computer readable media.

Other features and advantages of the invention are apparent from the following description, and from the claims.

BRIEF DESCRIPTION OF THE DRAWINGS

These and other aspects will now be described in detail with reference to the following drawings.

FIGS. 5A-E include images, graphs, and data tables obtained for a first study to evaluate an AS-OCTA implementation for detecting and determining ocular redness (OR) eye inflammation levels.

FIGS. 6A-F are images, graphs, and tables obtained for a second study to evaluate an AS-OCTA implementation for detecting and grading eye inflammation levels with vessel density semi-automated thresholding methods.

Like reference symbols in the various drawings indicate like elements.

DESCRIPTION

Figure 1:
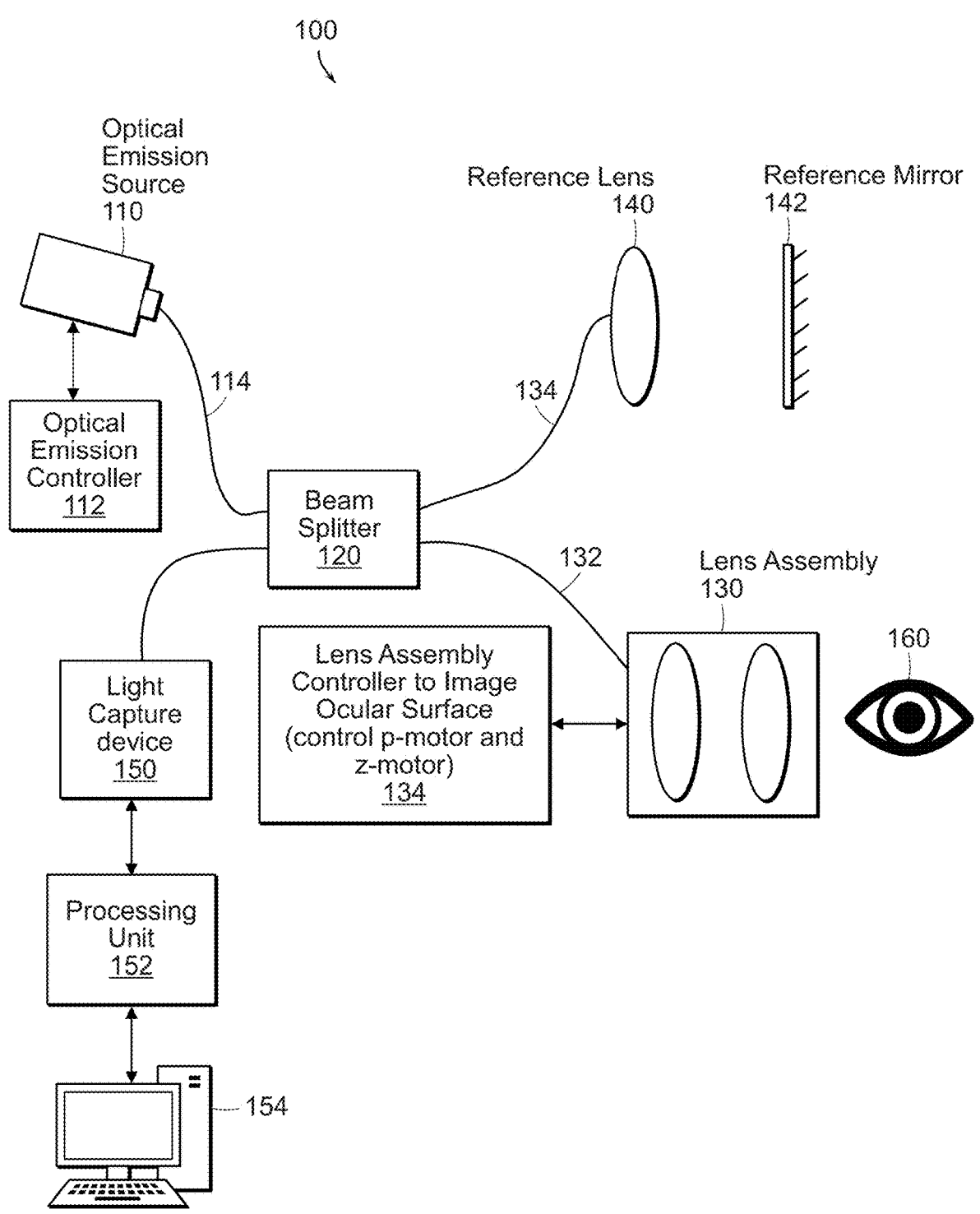
FIG. 1 is a schematic diagram of an imaging system to obtain and process blood flow image data for a patient's eye.

Disclosed are systems, devices, apparatus, methods and other realizations, to implement a non-invasive and fast approach, using anterior segment optical coherence tomography angiography (AS-OCTA) imaging, to detect blood flow in conjunctival microvasculature in a detailed and three-dimensional manner (depth and extension). Based on the acquired data representative of blood flow, blood vessel characteristics in the ocular surface are determined, from which an objective grading scale (also referred to as a metric, score, or measure) indicative of inflammation level in the eye (or some other organ) is derived. The implementations described herein thus provide a more objective and quantitative way of assessing ocular redness, and thus provide an objective way to represent inflammation level of the eye than can be achieved with subjective clinical grading (such as Efron, CCLRU, and/or Visakon scales). This approach provides a way of quantifying both local and systemic inflammation, including systemic medication reaction manifested on the eye surface (conjunctiva). For example, in some embodiments, anterior segment-OCTA (AS-OCTA) can be used to quantify vessel density (%), vessel diameter index, and fractal dimension parameters in a region of the eye (area of interest), with such measured parameters having direct association to ocular redness.

Accordingly, in some embodiments, a system is provided to determine inflammation levels of an eye of a patient. The system includes an imaging apparatus (e.g., an OCTA-based imaging apparatus) to determine blood flow characteristics at an ocular surface of an eye of the patient, and a controller configured to determine characteristics of blood vessels at the ocular surface of the eye based on the determined blood flow characteristics, and derive one or more systemic redness measures indicative of inflammation levels of the eye of the patient based on the determined characteristics of the blood vessels at the ocular surface of the eye. In some embodiments, the controller (e.g., a processor-based device) configured to determine the blood flow characteristics may be configured to perform anterior segment (AS) optical coherence tomography angiography (OCTA) for the ocular surface to detect blood flow at the ocular surface of the eye to produce images based on the detected blood flow representing a vasculature mapping at the ocular surface of the eye. The imaging data may be representative of blood flow image data for multiple layers of the ocular surface (e.g., the cornea, the limbus, the conjunctiva, the episcleral, the sclera, etc.), and the controller may thus be configured to separate the blood flow image data into separate blood flow image data sets for the respective multiple layers (e.g., based on filtering operations implemented with or without depth information associated with the acquired image data, and/or using learning machines). In some embodiments, the controller may also be configured to control operation of the imaging apparatus. For example, the controller may be configured to controllably adjust focus of a lens assembly coupled to the OCT imaging apparatus based on one or more of, for example, controllably actuating a focus-motor of the OCT imaging apparatus, and/or controllably actuating a z-motor of the OCT imaging apparatus. These embodiments are applicable to any available OCT system with different wavelengths, such as swept source OCT (1050 nm) or spectral domain OCT (840 nm). While laser penetration in the ocular tissue may differ (e.g., depending on the laser wavelength used), the analysis and interpretations of these generally follow a similar methodology. It may be possible, in some implementations (e.g., in imaging apparatus that utilizes tunable lasers or a swept source), to realize an OCT system with varying optical characteristics. Thus, in such implementations, the controller may be configured (e.g., through the same or different unit as the one controlling the lens assembly) to control an optical emission source as well as to control the activation and de-activation of the optical emission source, the focus, signal intensity, scan density, and/or other characteristics. Control of these characteristics allows for a way of controlling, among other things, the tissue penetration depth (i.e., for imaging purposes) and/or resultant image resolution.

Further, additional post-processing software to improve image resolution and decrease imaging artifacts can be applied. For example, projection-resolved processes may be applied to remove projection artifacts generated from the high flow intensity of the superficial vessels into the deeper layers to improve vascular visualization. Such processes may be configured to, in some embodiments, remove the smaller peaks throughout the scan that represent shadows of the overlying vessels, based, for example, on the decorrelation value and logarithm of reflectance intensity.

Eye inflammation is common and occurs in humans of all ages. It can last from a few minutes to years, depending on the type and severity of the underlying disease, disorder, or condition Inflammation can occur in one or both eyes at a time, and it may be accompanied by symptoms including itching, excessive tear production, and/or eye discharge. Additional potentially limiting symptoms of eye inflammation include pain, redness, swelling, tearing, and unusual warmth or heat (this is a non-exhaustive list). Inflammation can be caused by a variety of different causes. A non-exhaustive list of causes of eye inflammation include infection (e.g., bacterial, fungal, viral, or parasitic infection) (e.g., blepharitis, conjunctivitis, dacryocystitis, iritis, keratitis, periorbital cellulitis, scleritis and limbitis), allergy (e.g., drug allergies, food allergies, hay fever or allergic reaction to an allergen, and insect bite allergy)(e.g., chronic or acute allergy), autoimmune disorders (e.g., ankylosing spondylitis, Behcet's syndrome, dermatomyositis, Graves' disease, juvenile rheumatoid arthritis, multiple sclerosis, psoriatic arthritis, Reiter's syndrome, rheumatoid arthritis, Sjogren's syndrome, systemic lupus erythematosus, and Wegener's granulomatosis), graft versus host disease, dry eye syndrome, limbal stem cell insufficiency, irritation, and injury or trauma to the eye or eyelid (e.g., blunt trauma, corneal abrasion or ulcer, foreign objects or materials, hematoma, insect bite or sting, irritants, and orbital bone fracture). The treatment of eye inflammation typically administered to a subject will depend on the underlying cause of the disease. In some embodiments, the treatment can be, e.g., one or more of an eye lubricant (e.g., liquid or ointment), oral or topical antibiotic, an allergy treatment (e.g., an anti-histamine or cromolyn), and/or an immunosuppressive agent (e.g., a topical steroid or cyclosporine). The treatment prescribed to a patient, or the efficacy of a prescribed treatment, can depend upon the identification of the cause of the eye inflammation in the subject.

Subjects can be diagnosed as having eye inflammation by a medical professional (e.g., a physician, a physician's assistant, a nurse, a nurse's assistant, or a laboratory technician). As will be discussed in greater detail below, diagnosis and determination of a level of eye inflammation may be determined based on blood vessel characteristics at the ocular surface of a subject's/patient's eye, determined according to blood flow characteristics derived from image data produced through OCT-based procedures. The inflammation level measures determined according to some of the implementations described herein provide objective metrics that can be used to improve accuracy of medical studies (including studies to assess efficacy of possible treatments being performed). Further details regarding protocols and processes for conducting studies pertaining to eye inflammation and treatments therefor are provided, for example, in Patent Publication No. US 2013/0336557, entitled "INFLAMMATORY EYE DISORDERS," the content of which is hereby incorporated by reference in its entirety.

Subjects can be diagnosed as having eye inflammation and the intensity assessed with the ocular redness grading scales by a medical professional or trained technician (e.g., a physician, a physician's assistant, a nurse, a nurse's assistant, or a laboratory technician). These can further be compared to the blood vessel characteristics at the ocular surface of a subject's/patient's eye, determined according to blood flow characteristics derived from image data produced through OCT-based procedures. The inflammation level measures determined according to some of the implementations described herein provide objective metrics that can be compared to established ocular redness grading scales, evaluating their accuracy for medical studies (including studies to assess efficacy of possible treatments being performed).

In some of the embodiments described herein, a subject can be a child, a teenager, or an adult (e.g., at least 18, 25, 30, 40, 50, 60, 70, 80, or 90 years old). The subject can be a male or a female. A subject diagnosed as having eye inflammation may present with one or more (e.g., two, three, four, or any other number) of the symptoms and/or signs of eye inflammation described herein, and may have different range of blood-vessel-based measures, indicative of inflammation, than subjects in a different base characteristics (classified according to, for example, age, gender, race, etc.) Accordingly, a derived inflammation metric may need to be processed in some way (normalized or weighed) before a determination is made regarding the inflammation level severity indicated by the derived blood-vessel-based metric. A subject can be diagnosed as having eye inflammation based, in addition to or instead of the derived blood-vessel-based metric determined from OCT-based image data, on the detection of one or more ocular physical parameters using, for example, in vivo confocal microscopy. Thus, in some embodiments, confocal microscopy may be used as a complimentary tool in the process of determining, and assessing the severity of eye inflammation. Some in vivo confocal microscopy parameters that can be used to facilitate determination of eye inflammation include, for example, an elevation in the density of dendritic immune cells present in the cornea (e.g., in the center of the cornea), an elevation in the average size of dendritic immune cells present in the cornea (e.g., in the center of the cornea), an elevation in the average area covered by dendritic immune cells present in the cornea (e.g., in the center of the cornea), an elevation in the number or average density of dendritic inflammatory cells present in the peripheral cornea, an elevation in the hyperreflectivity of epithelial cells in the conjunctiva, an elevation in dendritic cell density in the conjunctiva, an elevation in the average dendritic cell size in the conjunctiva, an elevation in the number of hyperreflective dendritic cells in the conjunctiva, an elevation in the dilation of the lumen of blood vessels in the conjunctiva, an elevation in the average size of inflammatory cells in the blood vessels in the conjunctiva, an elevation in the sticking (elevation in the average time of transitory residence) of inflammatory cells to the blood vessels walls in the conjunctiva, an elevation in the average size of inflammatory cells in the lymph vessels in the conjunctiva, an elevation in the number of inflammatory cells present in the lymph vessels of the conjunctiva, an elevated ocular redness grading scale (derived based on blood vessel characteristics as determined using AS-OCTA imaging approach described herein), as compared to a reference level of the one or more ocular physical parameters.

Generally, the term "reference level" as described herein can be a threshold level or can be a level of the one or more ocular physical parameters in a healthy subject (e.g., a subject that does not have one or more symptoms of eye inflammation, or a subject that has not been diagnosed as having eye inflammation or an eye disorder) or the same subject at an earlier time points. Additional threshold values can be determined using methods known in the art or those described herein. Some of the description provided herein will be made with reference to a common cause of increased inflammation (for which accurate diagnosis, based, at least in part, on objective criteria or metric, as well an effective protocol for substantially accurately assessing efficacy of various treatment solutions is desired).

Thus, with reference to FIG. 1, a schematic diagram of a system 100, to obtain and process image data from which the blood flow information can be derived to generate vasculature mapping for the ocular surface and/or derive inflammation level for the eye, is shown. The system implementation described herein relies on optical coherence tomography (OCT) technology, which is a non-invasive imaging approach that uses low-coherence interferometry and provides high-quality images that allow anatomic and structural measurement of the anterior segment through OCT technology. OCT technology can be used to create En Face images (i.e., frontal sections cut of the desired tissue analyzed) and analyze the vessels of a specific tissue (angiogram). Optical coherence tomography angiography (OCTA) creates angiograms after ultra-high speed sequential B-scans of the same location. This allows the visualization of vessels based on detection of red blood cell flow through these sequential scans, thus creating three-dimensional mapping of this vasculature. Testing an evaluation of some of the implementations described herein showed that AS-OCTA can be used to identify conjunctival vessels and its characteristics in patients with ocular surface disease compared to healthy controls.

The imaging system 100 includes an optical emission source 110 comprising a low coherence light source. The light source may, for example, include a super-luminescent diode (e.g., when the imaging system 100 implements time-domain (TD) interferometry), or a fast sweeping laser source such as tunable laser (e.g., when implementing frequency-domain interferometry). An optical emission controller 112, which may be part of a controller (e.g., a processor-based controller) to control overall operation of the system 100, may be used to control the optical emission source, e.g., to control activation of the optical emission source, the frequency and illumination levels emitted by the optical emission source, scanning operations, and other functions to control the source emissions used in the OCT-based system. The generated illumination is directed by an optical waveguide 114, such as an optical fiber, to a beam splitter 120 configured to split and guide the optical radiation provided by the optical emission source 110 to a reference lens 140 that directs optical radiation to a reference mirror 142 (the reference lens and the reference mirror may collectively be referred to as the reference arm). The beam splitter 120 also directs the optical radiation from the optical emission source to a lens assembly 130 (comprising one or more of at least one lens, a scanning mirror, and/or scanning optics) that illuminates a physical object (in this case, a patient's eye 160; the lens assembly 130 and the illuminated object are also referred to as the object arm). The optical radiation may be directed to the reference lens 140 and/or the lens assembly 130 via separate waveguides (such as optical fibers) 142 and 132, respectively. In embodiments that implement the time-domain interferometry approach, the reference lens 140 is typically a scanning reference lens (or mirror). In embodiments in which the system 100 implements a frequency domain interferometry approach, the reference lens 140 is typically a fixed lens.

As further depicted in FIG. 1, the lens assembly 130 is in communication with a lens assembly controller 134 configured to control the configuration and attributes (e.g., focal depth) of the lens assembly 130 in order to control the specific tissue that is being scanned. The controller 134 (which may be part of the same circuitry or device that also implements the optical emission controller 112, or may be a separate independent controller device) may be configured to controllably adjust focus of the lens assembly 130 coupled to the OCT imaging system based on one or more of, for example, controllably actuating a focus-motor of the OCT imaging apparatus, and/or controllably actuating a z-motor of the OCT imaging apparatus to control the distance between the lens assembly and the eye of the patient. The control of the focus of lens assembly (to actuate the z-motor or p-motor) may be performed automatically by the controller 132 by automatically implementing autofocus functionality (e.g., measuring the distance between the lens assembly and the tissue to be processed, and actuating the motors of the lens assembly accordingly).

In some embodiments, controlling the characteristics of the system 100 to allow efficient and precise analysis of the ocular surface may be achieved through control of the optical emission source, realized through (for example) the controller 112 (and/or through the controller 134), which may be configured to adjust tissue penetrance characteristics of light optical radiation directed to the eye of the patient. For example, the wavelength/frequency characteristics of the optical emission source 110 can be adjusted to control the wavelength of the optical radiation directed to the lens assembly 130 and the reference lens 140. In some embodiments, the lens assembly controller 134 and/or the optical emission controller 112 can select the wavelength emitted by the optical emission source 110. For example, in implementations that use a tunable laser source (e.g., in frequency-domain OCT implementations), control of the emission source may be performed by controlling configuration of optical filters coupled to the tunable laser, by controlling the temperature of the tunable laser, or by controlling (via electrical or mechanical actuation) various other characteristics of the tunable laser, to thus control the light reflectance behavior of the optical radiation illuminating the target tissue to more optimally obtain and process information about tissue at the ocular surface of the eye. Similar or analogous control functionality may be applied to other types of emission sources, such as LED-based emission sources.

Collected light scattered from the eye 160 is combined with the reference light returning from the reference mirror 142 (via the reference lens 140) using, for example, a fiber coupler (which may be implemented as part of the beam splitter 120, or in a separate module) to form light interference patterns captured or detected in a light capture device 150 such as a camera or some other type of optical sensor (e.g., a charge-couple device (CCD)-type camera, a CMOS-based image sensor, etc.) to produce still or moving images that may be displayed on a user interface device and/or may be stored on a storage device or medium (a memory device). The output from the detector/light capture device 150 may be supplied to a processing unit 152 to process the data. The processing unit 152 may be part of a computing-based device (local or remote) 154 that may include a display device (e.g., an LCD monitor) on which the captured image data can be displayed. The processing unit 152 may be part of a controller circuitry to control the operation of the system 100, with such controller circuitry possibly include the optical emission controller 112 and lens assembly controller 134 of the system 100.

The combination of reflected light from the sample and the reference light from the reference mirror produces an interference pattern, which includes information about scattering intensities at different depths. In spectral domain OCT, the interference pattern represents a reflectivity profile (as a function of depth) of the sample (such a scan is referred to as an A-scan), based on which spatial information about the sample can be derived. Cross-sectional tomography data, or B-scan, can be derived by combining a sequence of A-scans, resulting in angiograms after sequential B-scans of the same location. In the example embodiments described herein, the sequential scans of the ocular surface provide a representation of red blood cell flow, thus creating three-dimensional mapping of this vasculature.

Thus, the AS-OCTA imaging performed by the system 100 (configured to direct the optical radiation at the region corresponding to the ocular surface of a patient's eye) provides data representative of the 3D structural features of the ocular surface. Based on this representation, blood vessel characteristics (e.g., morphology, density, etc., with such characteristics being optionally computed for different layers comprising the ocular surface) are derived. As noted, the blood vessel characteristics vary according to inflammation level at the ocular surface, and thus such blood vessel characteristics can be indicative of the inflammation level at ocular surface and/or at other parts of the patient's body.

Determination of blood vessel characteristics may be performed, in some embodiments, through application of various processing/filtering procedures (performed at the processing unit 152 and/or the computing-based device 154) that may have been specially developed to process images produced by AS-OCTA, or, alternatively, through application of various processing/filtering procedures obtained from open source libraries, e.g., through ImageJ open sources software. In some embodiments, generated B-scan image data may be processed according to one or more image processing procedure to derive metrics such as blood vessel characteristic (in the aggregate, or per layer or tissue thickness) such as blood vessel density, average blood vessel diameter, blood vessel branching pattern (derived as an index, vector, or other representation corresponding to the branching pattern), etc.

For example, to measure vessel density, local thickness of the vessels is computed (e.g., by using a geometry-to-distance-map procedure implemented, for example, with a Vessel Analysis plugin of an ImageJ tool, or by using some other tool), from which the vessel density can be computed and expressed as a percentage value corresponding to number of pixels representing vessels, divided by the total amount of pixels in the image. Thus, in such examples, the processing unit configured to process the one or more images obtained by the imaging system 100 is configured to identify pixels, for a particular image, representing blood vessels in the image, determining a ratio of the identified pixels representing the blood vessels in the image and total number of pixels in the particular image, and determining the vessel density based on the determined ratio. The processing unit configured to identify the pixels may be configured, in some examples, to binarize the particular image to convert pixel values into either a pre-determined pixel value representing blood flow (e.g., a value resulting in a white pixel), or another pre-determine pixel value representing no blood flow (e.g., a value resulting in a black pixel). For example, in a preliminary study using AS-OCTA in dry eye disease, ocular allergies and contact lens wearers, the vessel density in these inflammatory diseases ranged from 29.8% to 48.8% with a mean±standard deviation of 36.5±4.7%. In controls, the VD range was 26.1 to 36.5% with a mean±standard deviation of 31.1±2.5%.

In another example procedure, diameter attributes (e.g., average diameter) of the blood vessels represented in the image data can be determined. To assess the diameter of these vessels, a vessel diameter index may be derived by dividing the percentage of white pixels/per total pixels in binarized images by the percentage of white pixels/total pixels in skeletonized images. Skeletonization is a process for reducing foreground regions in a binary image to a skeletal remnant that largely preserves the extent and connectivity of the original region while throwing away most of the original foreground pixels. The skeletonization procedure thus reduces binary objects to 1 pixel wide representations. Accordingly, in such embodiments, the processing unit configured to process the one or more images obtained by the system 100 is configured to identify pixels, for a particular image (from the one or more images obtained or generated by the system 100), representing non-vessel objects in the particular image, generating a skeletonized image corresponding to the particular image comprising skeleton representations of blood vessels appearing in the particular image, identify skeletonized pixels, for the skeletonized image, representing non-vessel objects in the skeletonized image, and deriving a vessel diameter index based on the identified pixels representing the non-vessel objects in the particular image and the identified skeletonized pixels representing the non-vessel objects in the skeletonized image. In examples, the vessel diameter index is determined by the skeletonized pixel density to the vessel pixel density, which ranged in ocular surface inflammatory diseases from 2.30 to 3.51 with a mean±standard deviation of 3.06±0.21%, in the aforementioned study. In controls, the VDI ranged 2.49 to 3.14 with a mean (±standard deviation) of 2.89±0.16.

Another potential morphologic biomarker is based on analyzing the fractal dimension of the vessels, which is a measurement of vasculature branching pattern complexity. Fractal dimension can correlate with the severity of microvascular changes. Thus, in some embodiments, the processing unit configured to process the one or more images obtained by the system 100 is configured to perform fractal dimension analysis of vessels of the ocular surface appearing in the one or more images to determine vasculature branching pattern complexity of the blood vessels at the ocular surface of the eye. In the previously mentioned example studies, the mean±standard deviation fractal dimension was 1.637±0.020 with a 1.590 to 1.682 range using the fractal box count method, where 0 is least complexity and 2 represents most complexity. In controls, the mean±standard deviation was 1.624±0.026 with a 1.566 to 1.642 range.

Other processes/procedures, including other image processing procedures applied to image data obtained through the OCT-based imaging performed by the system 100 of FIG. 1 may also be used to derive other metrics, scores, or values, representative of the blood vessel characteristics captured by the image data. As noted in some embodiments, the image data that is obtained corresponds to blood flow image data in a three-dimensional space, namely, the three-dimensional space of the ocular surface. In such embodiments, the image data can be processed (based on the detected blood flow characteristics) to produce a representation of the three-dimensional vasculature distribution at the ocular surface of the eye. The three-dimensional space of the ocular surface generally corresponds to multiple surfaces of the ocular surface such as the cornea, the limbus, conjunctiva, episcleral, and/or the sclera. In some examples, determining blood vessel characteristics per layer can provide additional information on potential inflammation present in the eye or body (e.g., anomalous blood vessel characteristic at the ocular surface's superficial layer(s) (conjunctival vessels), but without similar anomalous behavior detected in the more inner layers of the ocular surface may indicate that there is a systemic response rather than a local response that can be directly related to the severity and cause. Thus, in such embodiments, the system 100 is further configured (e.g., through processing performed, for example, at the processing unit 152) to separate the blood flow image data into separate blood flow image data sets for the respective multiple layers. Subsequently, processing/filtering procedures, such as those described herein to derive blood vessel characteristics (e.g., to determine vessel density, average vessel diameter, branching pattern indicator, etc.) may be performed independently for each of the separated layers. In some embodiments, blood vessel characteristics may be first be determined collectively for the 3D image data obtained through the OCT-based imaging applied to the ocular surface, and subsequently the individual blood vessel characteristics for the various layers (or sets of layers, each comprising one or more ocular surface layers) may be computed.

In some implementations, image data for the one or more divided layers (e.g., corresponding to the different anatomical structures of the ocular surface) can be divided into one or more of a superficial layer, or a deep layer. For example, the superficial layer of the ocular surface can be identified from the epithelial layer until the transition of the conjunctival and the anterior limbal arcades with the episcleral and intrascleral vessels. The deep layer can be defined as having the aforementioned transition until the full thickness of the sclera. The transition can be determined by the vessel characteristics and their anatomical location. In order to determine at which depth this transition occurs, graders can be used to recognize these vascular plexi, and define the border between the superficial and deep layers in the images for comparison. Alternatively, a machine learning implementation may be used to recognize vascular plexi. By separating the blood vessel data into superficial or deep layer grouping, further information about inflammation levels and/or conditions associated with the specific blood vessel characteristics determined in such layers may be gleaned. That is, the blood vessel characteristics found at the superficial layer and/or deep layer may be further indicative/representative of the degree and location of inflammation in the eye certain conditions that might afflict the patient (e.g., a much higher blood vessel density x found at the superficial layer, in comparison to x blood vessel density at the deep layer, may indicate the inflammation in the eye is the result of a condition localized to the surface of the eye; whereas a high blood vessel density x found at both layers may indicate a more diffuse and severe inflammation). Separating the information obtained from AS-OCTA approaches into superficial and deeper layer groupings may provide additional novel approaches (not possible by other imaging methods thus far) to diagnose and identify characteristics that may be specific to certain diseases and/or conditions of the ocular surface.

Separating the blood flow image data obtained through the OCT-based imaging into multiple images (or data sets) corresponding to multiple layers (or sets of layers) of the ocular surface may be performed based on several possible procedures. For example, in some embodiments, the image data obtained through the OCT-imaging system 100 may include depth information acquired through volumetric imaging (e.g., obtaining the image data from at least two different vantage points, or observations, of the ocular surface). In another example, the separate, layered, image data may be generated based on machine learning techniques. In the latter approach, a learning engine may have been trained (using training input samples whose corresponding desired output is known or pre-determined) to produce layered output images responsive to the input image corresponding to the 3D space of the ocular space. Subsequent real input data may then be processed by the learning engine to produce output data consistent with the way the learning engine may have been trained. Thus, in such embodiments, the imaging system 100 may include a learning engine to separate input data corresponding to a 3D representation of red cell blood flow in vessels of the ocular surface into separate layered 3D output images corresponding to individual layers of the ocular surface. The separated output data corresponding to individual layers of the ocular surface may then be processed in a manner similar to that described above to derive blood vessel characteristics (based on which measures or metrics of inflammation level of the eye or other organs may be derived).

In some examples, blood vessel characteristics per layer of the ocular surface may be derived from the 3D image data produced for the entirety of the 3D space corresponding to the ocular surface (i.e., without first separating the 3D image data into individual ocular surface layers). The subsequent separation of computed blood vessel characteristics into values representative of such characteristics per layer may be done according to depth information that may be available for the image data (e.g., if stereoscopic imaging is employed), using a learning engine (e.g., trained to split blood vessel characteristic into multiple sets of characteristics, each corresponding to one or more layers of the ocular surface), or based on some other approach.

As noted, in some implementations, a learning engine may be used to either separate image data (representing the 3D space of the ocular surface) into multiple image data sets each representing blood flow image data in respective ones of multiple layers, or may be used to separate already derived blood vessel characteristics into respective blood vessel characteristic sets for such multiple layers. In embodiments in which the system 100 includes a machine learning implementation, such an implementation may be configured to iteratively analyzes training input data and the input data's corresponding output, and derive functions or models that cause subsequent inputs to produce outputs consistent with the machine's learned behavior. For example, and as noted, initially a training data set provided to the machine learning implementation of the system 100 may be used to define the response of the learning machine. The training data set can be as extensive and comprehensive as desired, or as practical. At the end of the learning process, the learning machine is ready to accept input, such as 3D image data representation of the ocular surface, and produce multiple image data representations of blood flow characteristics (or provide blood vessel characteristics) in individual layers of the ocular surface. In some embodiments, a machine learning implementation may be configured to process input data based on pre-defined procedures (e.g., adaptive processing and/or computations).

In some examples, the learning machine may be implemented as a neural network. Neural networks are in general composed of multiple layers of transformations (multiplications by a "weight" matrix), each followed by a linear or nonlinear function. The transformations are learned during training by making small changes to the weight matrices that progressively make the transformations more helpful to the final classification task (e.g., classification of input 3D image data into multiple layer image data, or classification of blood vessel characteristics for a 3D space of the ocular surface into blood vessel characteristics for individual layers constituting the ocular surface). The layered network may include convolutional processes, which are followed by pooling processes along with intermediate connections between the layers to enhance the sharing of information between the layers. Examples of neural networks include convolutional neural network (CNN), recurrent neural networks (RNN), etc. Convolutional layers allow a network to efficiently learn features that are invariant to an exact location in a data set by applying the same learned transformation to subsections of the entire data set. Other examples of learning engines that may be implemented as part of the system 100 may include a support vector machine, decision trees techniques, regression techniques, and/or other types of machine learning techniques.

Having determined blood vessel characteristics (be it collectively for the entire 3D space of the ocular surface, or for individual layers), one or more ocular redness grading scales (also referred to as a metric, score, or measure) indicative of inflammation levels of the eye of the patient based on the determined characteristics of blood vessels at the ocular surface of the eye are derived (e.g., subjective grades such as mild, moderate, severe, etc., or grades such as 1, 2, 3 etc.) In some examples, the characteristics/ attributes obtained (e.g., the vessel density, or average vessel diameter) can be used as the metric indicative of the ocular redness scale. Alternatively, a combination of derive characteristics can be used to compute a composite value that is a function of the different characteristics (e.g., a weighted sum or average of the different computed characteristics, such as the vessel density, average diameter, pattern complexity, etc.) In some embodiments, the determination of the grading scale may also be implemented via a learning engine. For example, blood vessel characteristics (represented as a data set, or vectors, that include values corresponding to the various blood vessel characteristics determined, such as blood vessel density, average diameter, or any other metric) are fed into a trained learning machine/engine that has previously been trained with input data samples that include blood vessel characteristics and a corresponding output representative of ocular surface grading scale or measure indicative of an inflammation level. Such output grading scale (for the respective input data of blood vessel characteristics) may have been determined based on one or more tests that represent inflammation level (e.g., blood test showing increased white blood cells levels), the presence of various types of cells in the cornea (hyperreflective superficial epithelial, dendritic immune cells, etc.), expert determination of whether inflammation (with or without a grading scale) is present, and so on. In embodiments in which the output inflammation level of training data is based on the presence of various cell types in the cornea, such output data can be determined through confocal microscopy imaging of the cornea at different time instances to determine one or more of, for example, (i) a density of dendritic immune cells present in the cornea, (ii) the average size of dendritic immune cells present in the cornea, (iii) the average area covered by dendritic immune cells present in the cornea, and so on. Further details about the use of confocal microscopy on the cornea are provided in U.S. application Ser. No. 13/971,609 (U.S. PG Publication No. 2013/0336557), entitled "Inflammatory Eye Disorders," the content of which is hereby incorporated by reference in its entirety.

Figure 2:
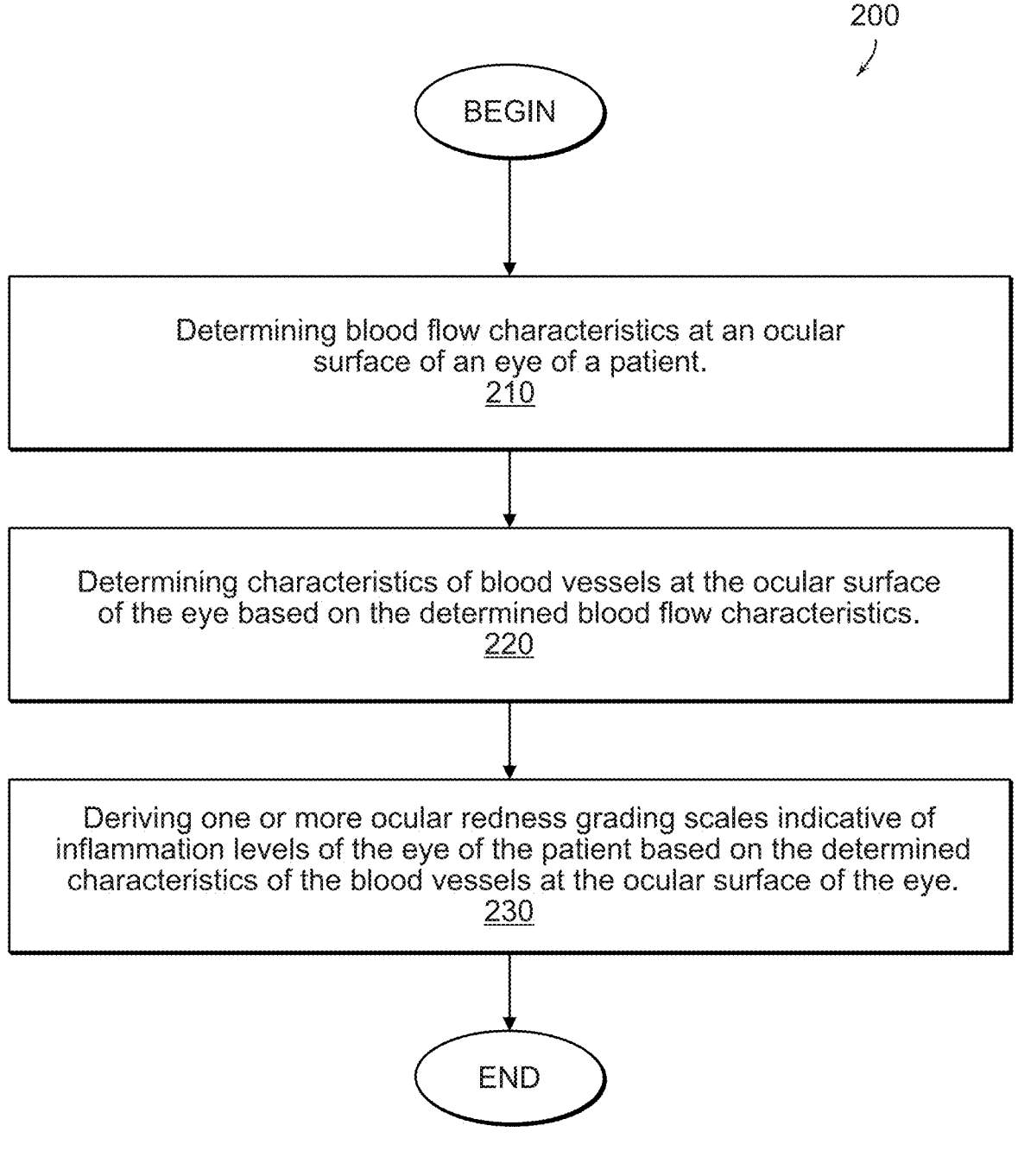
FIG. 2 is a flowchart of an example procedure to determine ocular redness grading scales from blood vessel characteristics determined using OCT-based imaging.

With reference next to FIG. 2, a flowchart of an example procedure 200 to determine ocular redness grading scales from blood vessel characteristics determined using OCT-based imaging is shown. The procedure 200 includes determining 210 blood flow characteristics at an ocular surface of an eye of a patient. As noted, in some embodiments, determining the blood flow characteristics at the ocular surface of the eye may include performing (e.g., using an imaging system such as the system 100 of FIG. 1) anterior segment (AS) optical coherence tomography angiography (OCTA) imaging for the ocular surface to detect blood flow at the ocular surface of the eye. Performing AS-OCTA imaging for the ocular surface may include producing images based on the detected blood flow representing a vasculature distribution at the ocular surface of the eye. For example, in some implementations, images may be obtained on a spectral domain OCTA system, such as Avanti XR AngioVue (Optovue Inc., Freemont, CA) to perform 6×6 mm HD Retina scan used with an Optovue anterior segment lens (Cornea Adaptive Module Long) and manual or automated adjustments to set the focus on the conjunctival surface. In such implementations, the system may acquire volumetric scans of 304×304 A-scans at 70,000 A-scans per second, using, for example, a light source centered on 840 nm and a bandwidth of 45 nm. Flow can then be detected through motion contrast of repeated A-scans at the same location, with motion artifacts removed by 3D orthogonal registration and merging of 2 scans using an SSADA process. The PR process can then be applied to remove projection artifacts generated from the high flow intensity of the superficial vessels.

In some embodiments, performing AS-OCTA imaging for the ocular surface to detect blood flow at the ocular surface of the eye may include obtaining blood flow image data for multiple layers of the ocular surface, with the multiple layers including one or more of, for example, the cornea, the limbus, the conjunctiva, the episcleral, and/or the sclera, and also different depths within the above mentioned examples. In some examples, obtaining the blood flow image data the multiple layers may further include dividing the image data for at least one of the multiple layers, based on a respective reference depth for the at least one of the multiple layers (e.g., depending on whether the tissue layer corresponds to the cornea, the limbus, the conjunctiva, the episcleral, and/or the sclera, etc.), into one or more of a superficial layer image data or a deep layer data. For example, instead of dividing the image data per anatomical layer, the image data may be grouped according to different layer depth levels (e.g., superficial layer, deep layer, full thickness layer). In some embodiments, the blood flow data (e.g., image data) may be separated into data sets corresponding to respective layers of the ocular surface. For example, separating the blood flow image data into separate blood flow image data sets for the respective multiple layers may include separating the blood flow image data into the separate blood flow image data sets using machine learning techniques.

Performing AS-OCTA for the ocular surface may include, in some implementations, controllably adjusting focus of a lens assembly coupled to an OCT imaging apparatus based on one or more of, for example, controllably actuating a focus-motor of the OCT imaging apparatus, or controllably actuating a z-motor of the OCT imaging apparatus to control the distance between the lens assembly and the eye of the patient. In some examples, the control of the imaging functionality may also be achieved through control of light radiation characteristics (so as to control the penetration depth of the optical radiation). Thus, in such embodiments, performing AS-OCTA imaging for the ocular surface may include controlling an optical emission source of an OCT imaging apparatus to provide optical radiation controllably directed at the ocular surface, including performing one or more of, for example, controllably adjusting tissue penetrance characteristics of generated directed to the eye of the patient so that light reflectance behavior is affected (impacted) by tissue at the ocular surface of the eye (e.g., the reflectance is caused primarily by tissue at the ocular surface rather than deeper level tissue of the eye), and/or controllably actuating activation and de-activation of the optical emission source provided to the OCT imaging apparatus.

With continued reference to FIG. 2, the procedure 200 further includes determining 220 characteristics of blood vessels at the ocular surface of the eye based on the determined blood flow characteristics. In some embodiments, determining the characteristics of the blood vessels at the ocular surface may include determining vessel characteristics based the blood flow characteristics at the ocular surface of the eye. As discussed herein, there are various methodologies and techniques to characterize the blood vessels. For example, determining characteristics of the blood vessels at the ocular surface of the eye may include determining one or more of, for example, vessel density of the blood vessels at the ocular surface, diameter attributes of at least some of the blood vessels, and/or vasculature branching pattern attributes for the blood vessels as measured by fractal dimension. Such characteristics may be derived by obtaining one or more images representative of a vasculature mapping at the ocular surface of the eye based on the determined blood flow characteristics and processing the one or more images to determine the characteristics of the blood vessels based on resultant image data from the processed one or more images.

In example embodiments, processing the one or more images may include identifying pixels, for a particular image from the one or more images, representing blood vessels in the image, determining a ratio of the identified pixels representing the blood vessels in the image and total number of pixels in the particular image, and determining the vessel density based on the determined ratio. Identifying the pixels may include binarizing the particular image to convert pixel values into either a pre-determined pixel value representing blood flow, or another pre-determine pixel value representing no blood flow. In other example embodiments, processing the one or more images may include identifying pixels, for a particular image from the one or more images, representing non-vessel objects in the particular image, generating a skeletonized image comprising skeleton representations of blood vessels appearing in the particular image, identifying skeletonized pixels, for the skeletonized image, representing non-vessel objects in the skeletonized image, and deriving a vessel diameter index based on the identified pixels representing the non-vessel objects in the particular image and the identified skeletonized pixels representing the non-vessel objects in the skeletonized image. In further example embodiment, processing the one or more images may include performing fractal dimension analysis of vessels appearing in the one or more images to determine vasculature branching pattern complexity of the blood vessels at the ocular surface of the eye. Fractal dimension is a measurement that represents the complexity and branching of the vessels, which could represent characteristics of inflammation.

Turning back to FIG. 2, as shown, the procedure 200 further includes deriving 230 one or more ocular redness grading scales indicative of inflammation levels of the eye of the patient based on the determined characteristics of blood vessels at the ocular surface of the eye. The grading scales provide an objective (which depends on objective measurements performed via AS-OCTA-based imaging procedure) metric, scale, or score that can be used to assess the inflammation level of the eye (and/or of other parts of the patient's body), and can thus be used to diagnose medical conditions, assess the efficacy of various therapy, and so on (as will be described in greater detail below). In some examples, the ocular redness grading scales may be determined per layer (i.e., obtain separate grading scales for each of multiple layers comprising the ocular surface). The grading scales may be determined according to a formula that produces a scaler metric as a function of one or more blood vessel characteristics. Alternatively, the grading scales may be computed using a learning machine (e.g., implemented via a neural-net, or some other learning machine implementation) that was trained with training samples comprising example combinations of blood vessel characteristics (derived based on blood flow data obtained from AS-OCTA imaging of the ocular surface) and respective outputs of grading scales corresponding to inflammation levels that were independently determined for the training samples. In some examples, the actual blood vessel characteristics may be used as a metric or scale to represent the inflammation level. For example, a derived vessel density score can be used as a grading scale indicating the inflammation level.

Performing the various operations described herein may be facilitated by a controller system (e.g., a processor-based controller system). Particularly, at least some of the various devices/systems described herein, including any of the neural network devices, data acquisition devices (such devices/components constituting the imaging system 100), a remote server or device that performs at least some of the detection and/or analysis operations described herein (such as those described in relation to FIGS. 1-2) may be implemented, at least in part, using one or more processor-based devices.

Figure 3:
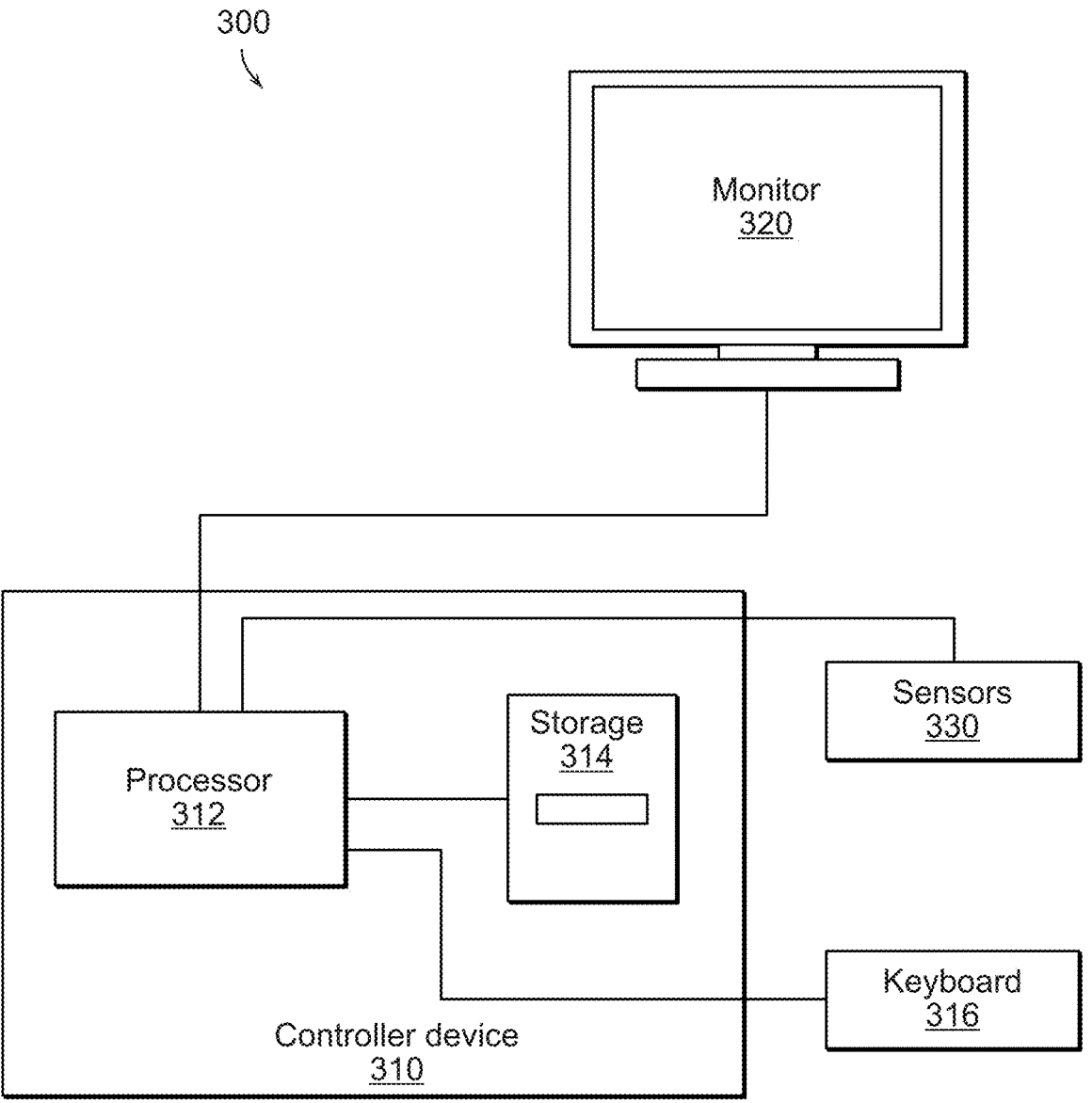
FIG. 3 is a schematic diagram of an example computing system.

Thus, with reference to FIG. 3, a schematic diagram of a computing system 300 is shown. The computing system 300 includes a processor-based device (also referred to as a controller device) 310 such as a personal computer, a server, a specialized computing device, and so forth, that typically includes a central processor unit 312, or some other type of controller (or a plurality of such processor/controller units). In addition to the CPU 312, the system includes main memory, cache memory and bus interface circuits (not shown in FIG. 3). The processor-based device 310 may include a mass storage element 314, such as a hard drive (realize as magnetic discs, solid state (semiconductor) memory devices), flash drive associated with the computer system, etc. The computing system 300 may further include a keyboard 316, or keypad, or some other user input interface, and a monitor 320, e.g., an LCD (liquid crystal display) monitor, that may be placed where a user can access them. The computing system 300 may also include one or more sensors 330 (e.g., an image-capture device to obtain OCT-based image data for the ocular surface, other types of sensors that may be used to control various components of the system 100, including, for example, to control the illumination source 110, to control the lens assembly 130, the senor arm of the system 100, and so on).

The processor-based device 310 is configured to facilitate, for example, the implementation of blood flow detection at an ocular surface of a patient's eye, determine blood vessel characteristics therefrom, and derive ocular redness grading scales (indicative of inflammation level of the patient's eye) based on the determined blood vessel characteristics. The processor-based device 310 may also be configured to facilitate determining the efficacy of treatments, conducting studies, selecting subjects for such studies, comparing measurements performed during such studies, and/or performing other procedures and methods as more particularly described herein. The storage device 314 may thus include a computer program product that when executed on the processor-based device 310 causes the processor-based device to perform operations to facilitate the implementation of procedures and operations described herein. The processor-based device may further include peripheral devices to enable input/output functionality. Such peripheral devices may include, for example, a CD-ROM drive and/or flash drive (e.g., a removable flash drive), or a network connection (e.g., implemented using a USB port and/or a wireless transceiver(s)), for downloading related content to the connected system. Such peripheral devices may also be used for downloading software containing computer instructions to enable general operation of the respective system/device. Alternatively, or additionally, in some embodiments, special purpose logic circuitry, e.g., an FPGA (field programmable gate array), an ASIC (application-specific integrated circuit), a DSP processor, etc., may be used in the implementation of the system 300 in order to implement the various procedures and methods described herein. Other modules that may be included with the processor-based device 310 are speakers, a sound card, a pointing device, e.g., a mouse or a trackball, by which the user can provide input to the computing system 300. The processor-based device 310 may include an operating system, e.g., Windows XP® Microsoft Corporation operating system, Ubuntu operating system, etc.

Computer programs (also known as programs, software, software applications or code) include machine instructions for a programmable processor and may be implemented in a high-level procedural and/or object-oriented programming language, and/or in assembly/machine language. As used herein, the term "machine-readable medium" refers to any non-transitory computer program product, apparatus and/or device (e.g., magnetic discs, optical disks, memory, Programmable Logic Devices (PLDs)) used to provide machine instructions and/or data to a programmable processor, including a non-transitory machine-readable medium that receives machine instructions as a machine-readable signal.

In some embodiments, any suitable computer readable media can be used for storing instructions for performing the processes/operations/procedures described herein. For example, in some embodiments computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as flash memory), electrically programmable read only memory (EPROM), electrically erasable programmable read only Memory (EEPROM), etc.), any suitable media that is not fleeting or not devoid of any semblance of permanence during transmission, and/or any suitable tangible media. As another example, transitory computer readable media can include signals on networks, in wires, conductors, optical fibers, circuits, any suitable media that is fleeting and devoid of any semblance of permanence during transmission, and/or any suitable intangible media.

Figure 4:
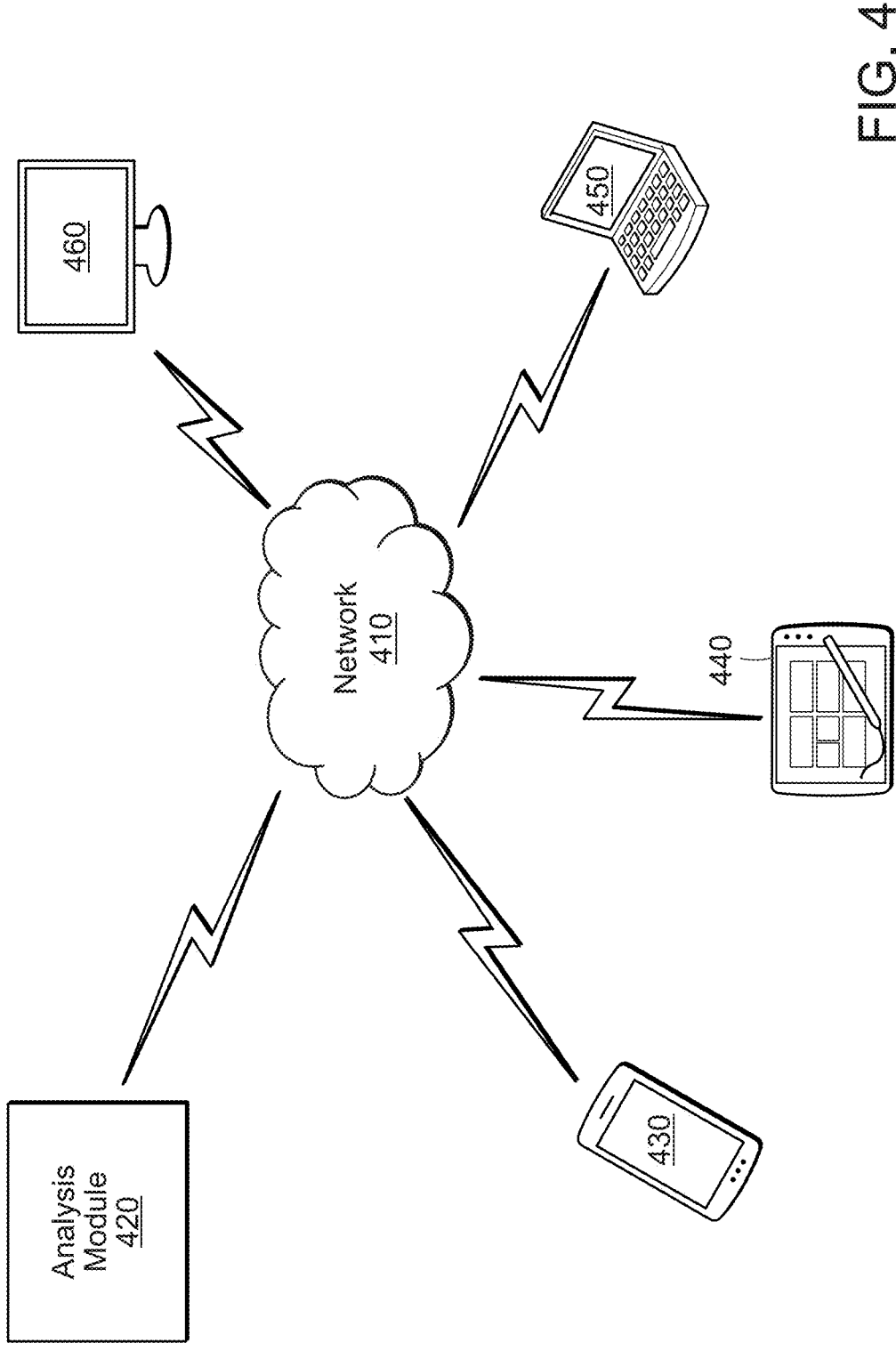
FIG. 4 is a diagram of an example environment used for implementing the methods and procedures described herein.

In some implementations, a network environment may be used implement the functionalities described herein (e.g., to derive ocular redness grading scale using AS-OCTA imaging, and to otherwise implement the functions and operations described in relation to FIGS. 1-8). An example of such a network environment 400 is shown in FIG. 4. As shown in the example of FIG. 4, the networking environment 400 provides users (e.g., individuals such as clinicians) access to information collected, produced and/or stored by an analysis module 420 (which may be similar to, in implementation and/or configuration, to the processing unit 152 and/or the computing-based device 154 of FIG. 1). For example, the analysis module may be an administered by an entity (or multiple entities) that employs one or more computing devices (e.g., servers, computer systems, etc.) to process information acquired from an AS-OCTA imaging system (such as the system illustrated in FIG. 1) to obtain OCT-based images (e.g., B-scans) representative of blood flow characteristics within the ocular surface. The computing devices may also have access to other types of data (e.g., confocal microscopy images) based on which indicators of the presence and/or levels of inflammatory eye disorders can be obtained. In some implementations, the analysis module 420 may execute one or more processes for analyzing OCT-based image data corresponding to the ocular surface in accordance with techniques described in this document. The analysis module 420 may also be configured to implement at least some of the other procedures and methods described herein to evaluate and process treatment data (including determining the efficacy of treatments, selecting subject for treatment studies, etc.)

Various techniques and methodologies may be implemented for exchanging information between the users and the analysis module 420. For example, one or more networks, such as a network 410 (e.g., a private network or a public network such as the Internet) may be employed for interchanging information with user devices. As illustrated in the figure, various types of computing devices and display devices may be employed for information exchange. These may include hand-held computing devices (e.g., a cellular telephone 430, a tablet computing device 440, etc.) that may exchange information through the one or more networks 410 with the analysis module 420. Other types of computing devices such as a laptop computer 450 and other computer systems may also be used to exchange information with the analysis module 420. A display device such as a liquid crystal display (LCD) 460 or other display device may also present information from the analysis module 420. One or more types of information protocols (e.g., file transfer protocols, etc.) may be implemented exchanging information. The user devices may also present one or more types of interfaces (e.g., graphical user interfaces) to exchange information between the user and the analysis module 420. For example, a network browser may be executed by a user device to establish a connection with a website (or webpage) of the analysis module 420 and provide a vehicle for exchanging information. The analysis module 420 can include software and hardware configured to analyze images in accordance with the description provided in this disclosure, and to perform the various procedures and methods described herein. Communication between various units or nodes of the computing environment 400, may be realized through wired communication (e.g., implemented via an ethernet protocol), and/or wireless communication (e.g., implemented through WLAN protocols, such as WiFi, or via WWAN communication technologies such as LTE, 5G, etc.)

The above methods, systems, and other implementations to derive an objective measure(s) of the inflammation level in the eye were tested and evaluated in several conducted studies and experiments. In a first study that was conducted based on the implementations described herein, the eyes of ten (10) healthy individuals (controls) and 10 individuals with mild inflammation were scanned using an AS-OCTA system implementation (similar to that depicted in FIG. 1). The same eye of each of these subjects was photographed for clinical ocular redness grading and comparison. The commonly used Efron scale, which ranges from 0 (normal) to 4 (severe redness), was used to make an initial assessment of ocular redness level. Example photos illustrating some common clinical grading scales, including the Efron scale, the CCLRU, the Annunziato, and the Visakon scales are provided, for example, in the publication by N. Efron et al. of "Validation of grading scales for contact lens complications," Ophthalmic and Physiological Optics, 2001 January; 21(1):17-29.

Figure 5A:
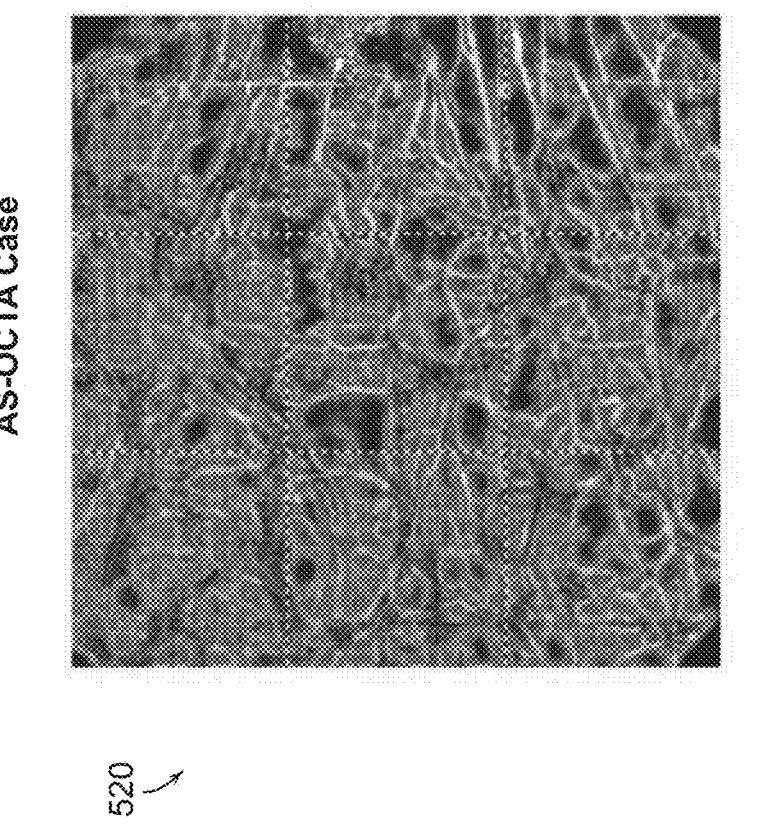
Figure 5A:
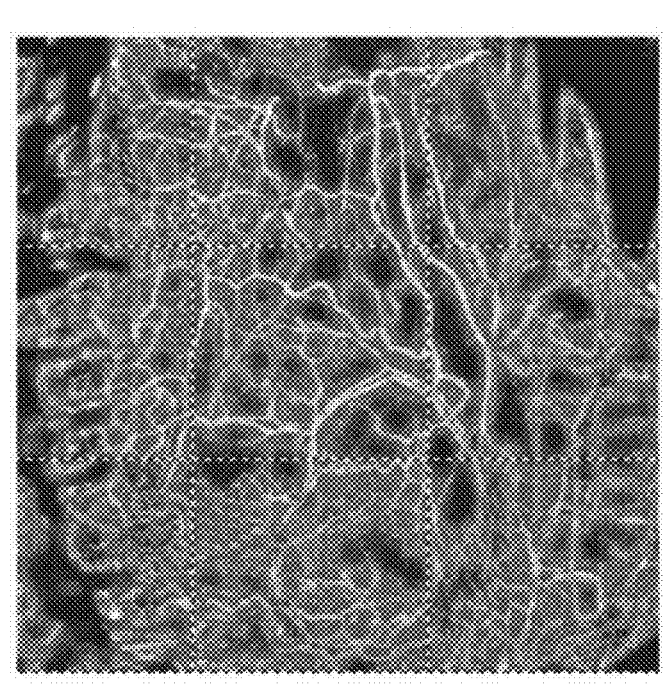
Figure 5B:
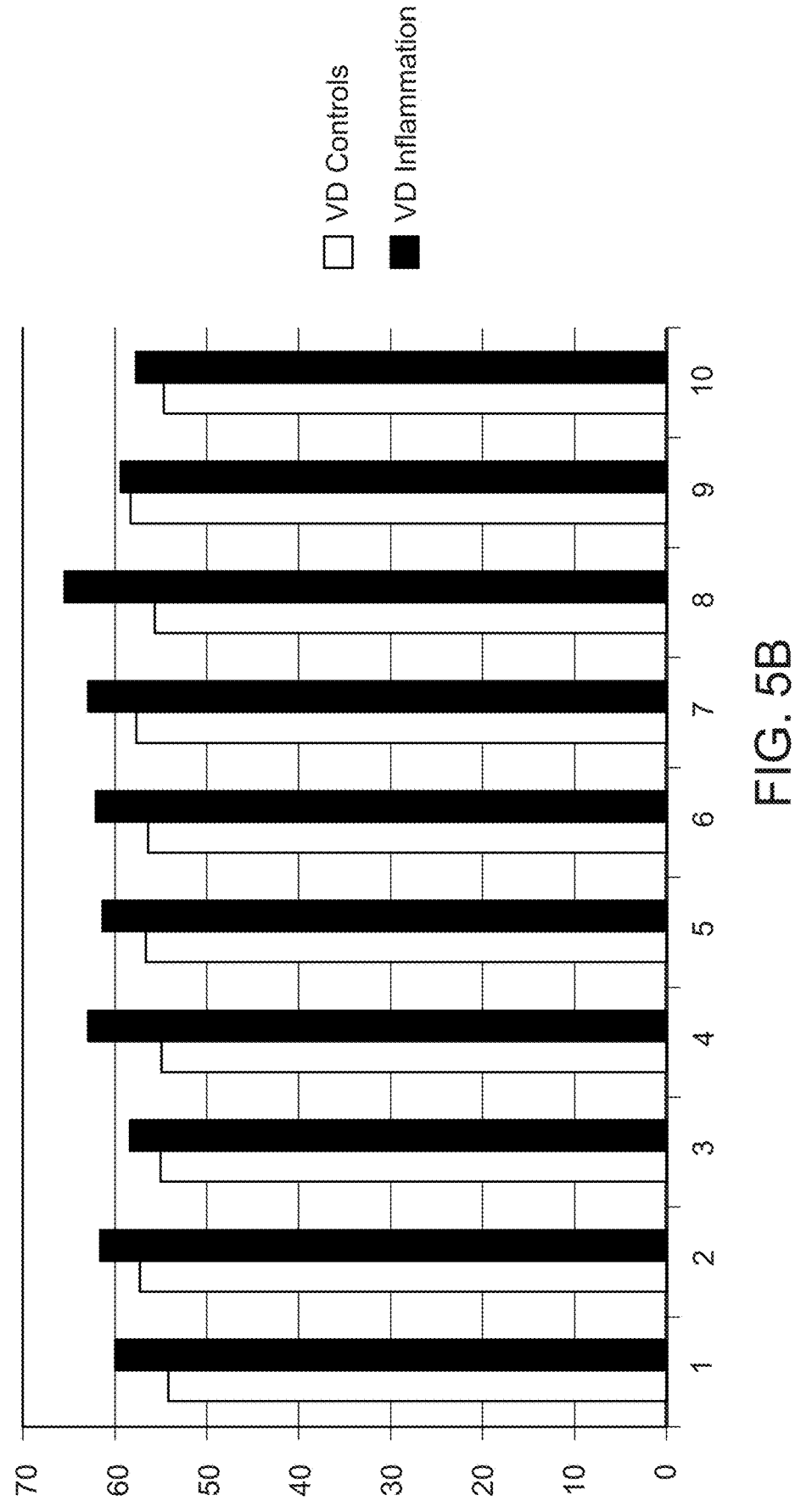
Figure 5C:

FIG. 5A includes two images 510 and 520 of example AS-OCTA scans from a healthy (control) individual, and an individual with mild eye inflammation, respectively. In the study, the AS-OCTA scans for the various individual were processed, and vessel densities were derived from those scans (processing techniques such as those described in the present disclosure to determine vessel density may be used). The mean vessel density derived from AS-OCTA scan in the controls group and the inflamed groups were 56.3%±1.3 and 61.0%±2.3, respectively (with $p<0.001$). FIG. 5B is a graph 550 presenting the vessel density results for all subjects. It is noted that the mean ocular redness grade (using the Efron scale) for the control group was 0.4±0.5, while for the mild inflammation group the ocular redness grade was 1.7±0.4 (p<0.001). FIG. 5C is a graph showing the ocular redness (OR) grading for the subjects that participated in the study (for some of the individuals in the control group, a grading value of 0 was assigned). FIG. 5D includes a table 562 providing the correlation between AS-OCTA VD and OR scores of the nasal, temporal and total conjunctiva.

Figure 5E:
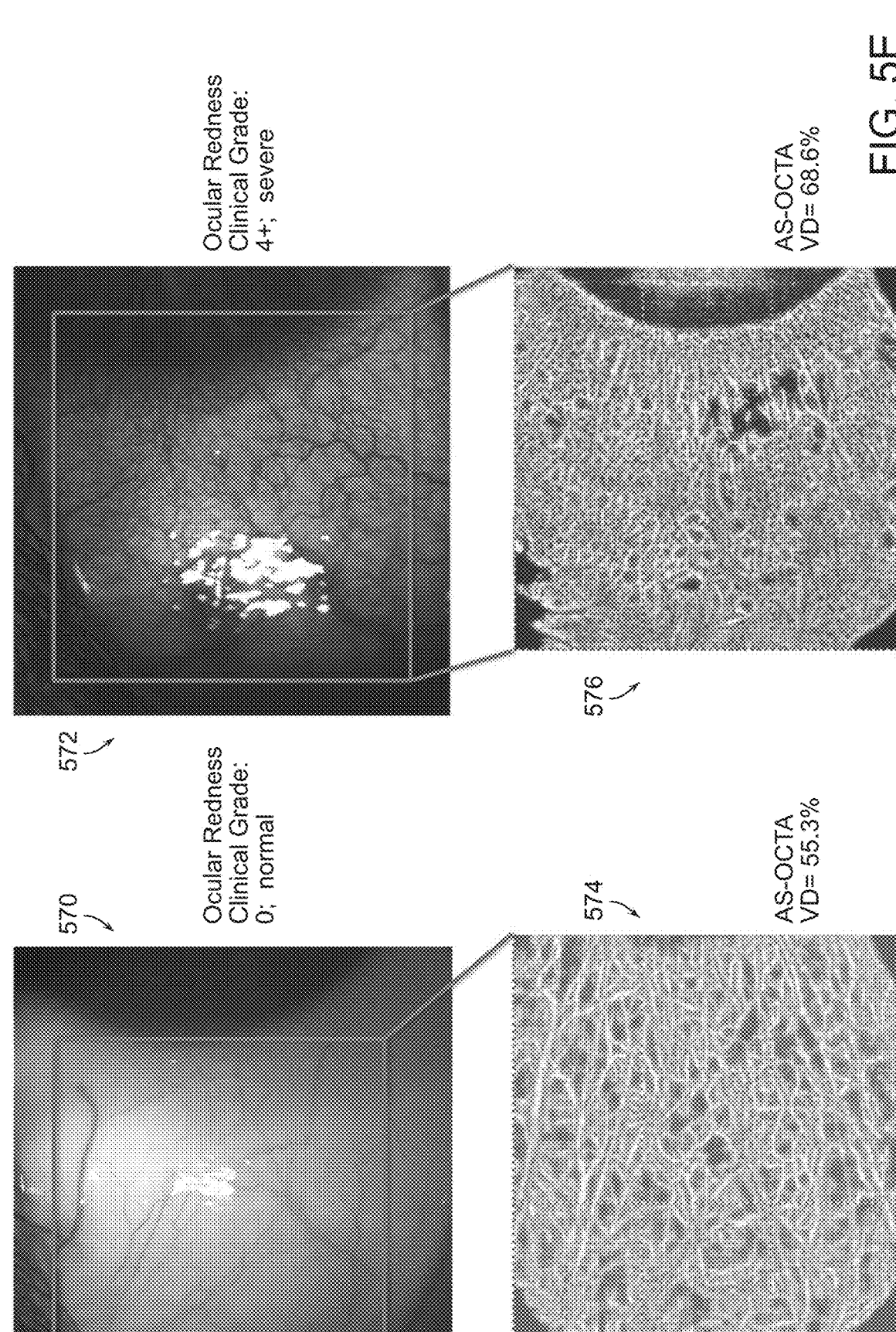

FIG. 5E shows a comparison of the eyes of two subjects (one with a healthy eye, as shown in the slit-lamp photo 570, and one with a severely inflamed eye, as shown in the slit-lamp photo 572), to their respective AS-OCTA scans (scan 574 for the healthy eye, and a scan 576 for the inflamed eye). Based on the AS-OCTA scans, vessels density values of 55.3% and 68.6%, respectively, were derived. Thus, it can be seen, based on comparison of the vessel density results to the ocular redness grading results in the study, that there is a good correlation between the ocular redness clinical grading scale (the conventional subjective scale such as the Efron scale), and the ocular redness grading scale that was based on a vessel density metric (specifically, in this study there was a correlation value of 0.76, with p<0.001).

Figure 6C:
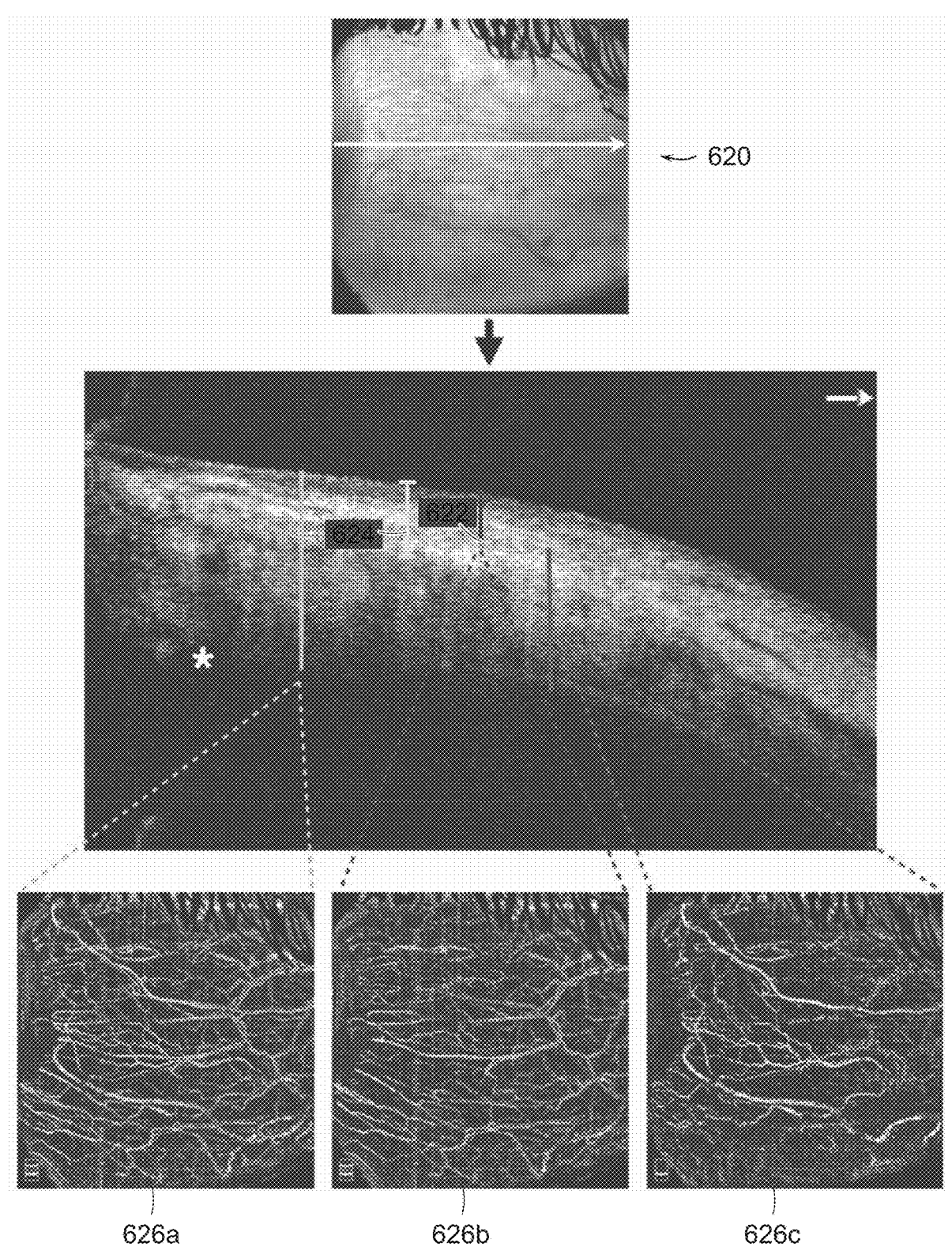

FIGS. 6A-F provides images and data obtained for another study. AS-OCTA Images obtained for this study were obtained through a spectral domain OCTA system, namely, the Avanti XR AngioVue (Optovue Inc., Freemont, CA). FIG. 6A is a table 600 (marked as Table 1) providing experimental data in relation to various conditions (arranged in columns). The data corresponds to descriptive and parameter distribution between the controls, contact lens wear (CLW), dry eye disease (DED) and acute ocular inflammation (AOI) groups. In the Table 1 of FIG. 6A, VD represents measured vessel density, VDI is vessel diameter index, and FD represents the fractal dimension.

FIG. 6B is another table complied for the study (Table 2, marked 610) providing distribution between nasal and temporal vessel density (VD), vessel diameter index (VDI) and fractal dimension (FD) between the controls, contact lens wear (CLW), dry eye disease (DED) and acute ocular inflammation (AOI) groups.

FIG. 6C includes images for a temporal left eye scan of a healthy control with a right gaze. An image 620 is an enface OCT scan where the corneascleral limit (white dashed lines) and eyelashes (black lines) are shown. The line 622 shows the location where the vessel cutoff depth was measured, and a location 624 indicates where the conjunctival thickness was measured. The white asterisk shows the location of the iris implantation. The images 626a, 626b, and 626c correspond to the AS-OCTA segmentation for full thickness, superficial plexus and deep plexus, respectively.

Figure 6D:
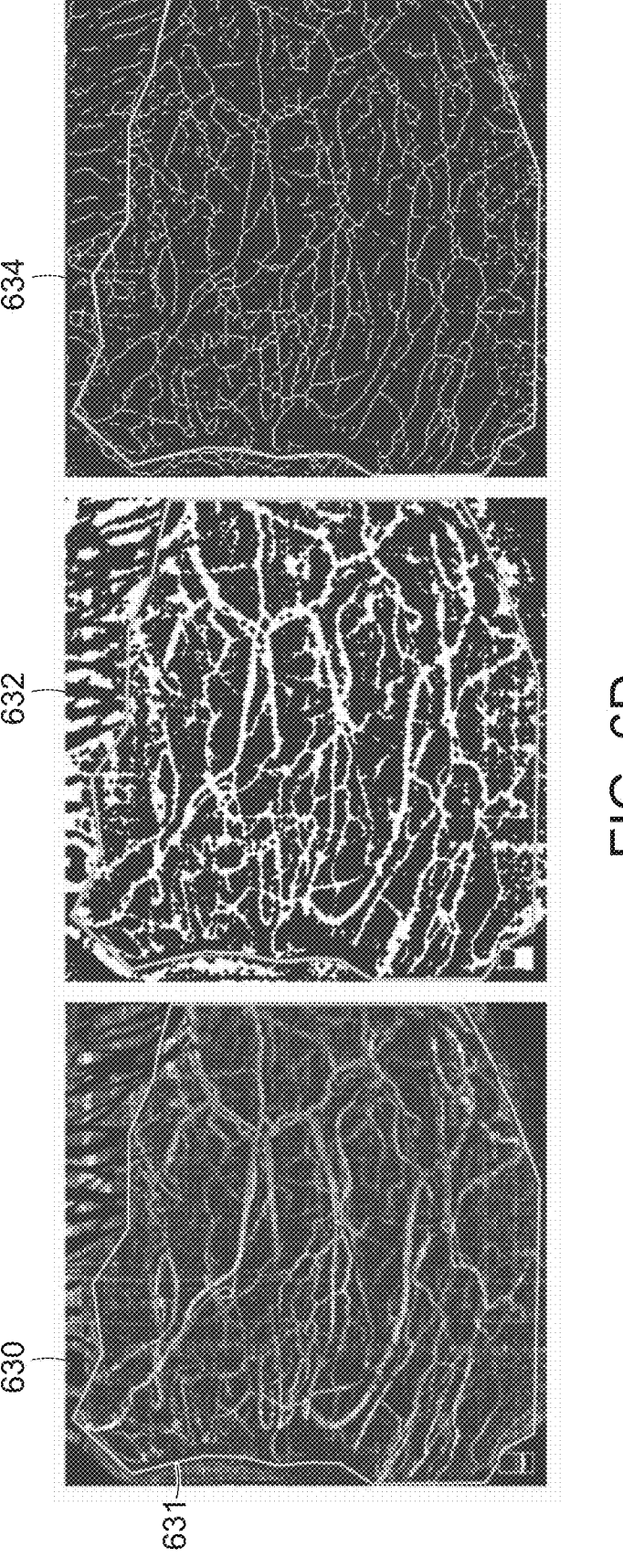

FIG. 6D includes AS-OCTA images 630-634. Image 630 (the left-most image) is an AS-OCTA image of temporal left eye. The middle image 632 is a binarized image of the AS-OCTA, while the right image 634 is a skeletonized image of the binarized image. The various outlines appearing in the images (e.g., the outline 631 of the image 630) represent the selected area of interest for the vessel analyses.

Figure 6E:
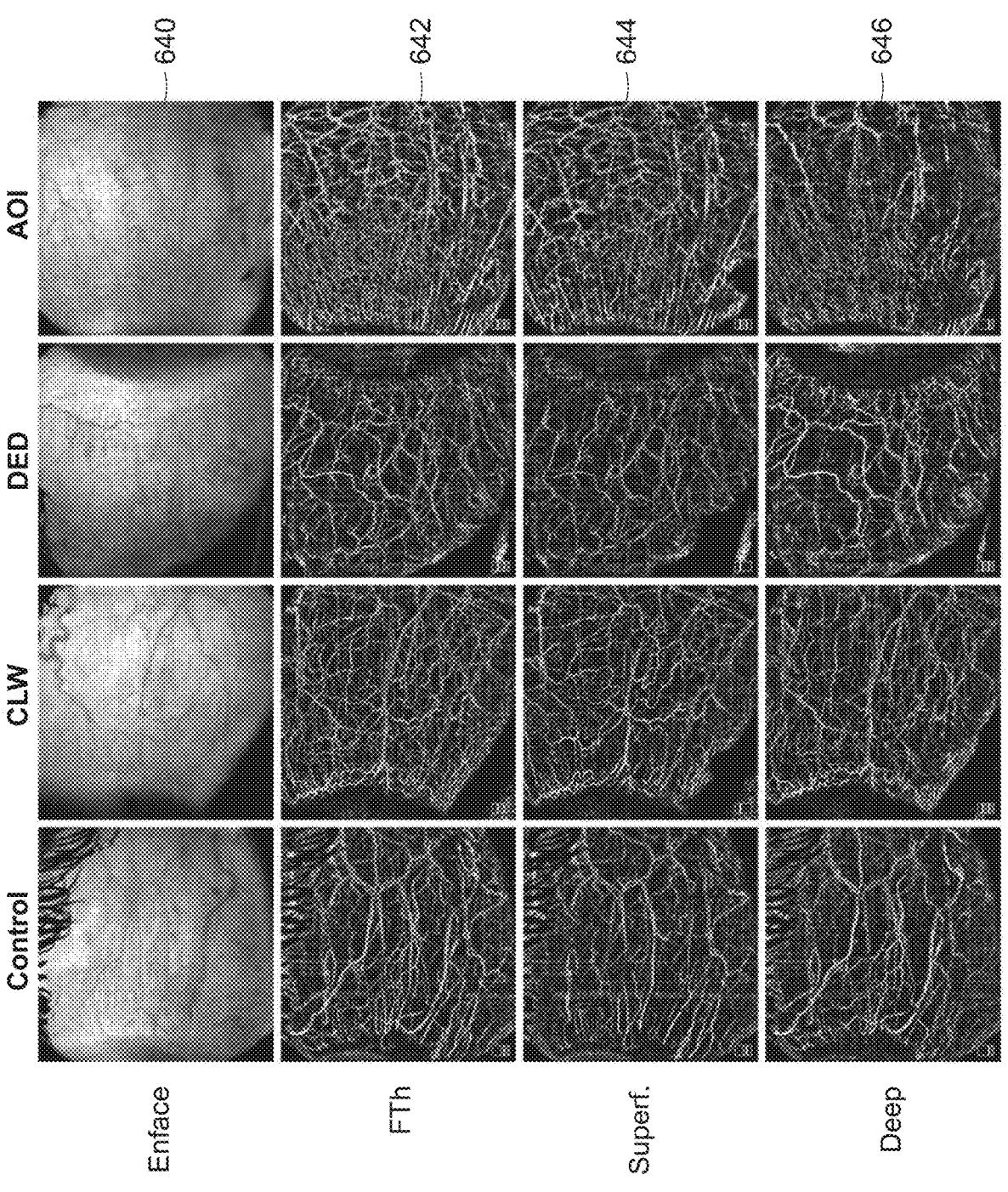

FIG. 6E includes representative images of the control, contact lens wearer (CLW), dry eye disease (DED), and acute ocular inflammation (AOI) groups with their en face OCT (first row, marked as row 640), full thickness AS-OCTA (FTh; second row, marked as row 642), superficial AS-OCTA (superf.; third row, marked as row 644) and deep AS-OCTA (fourth row, marked as row 646).

Figure 6F:
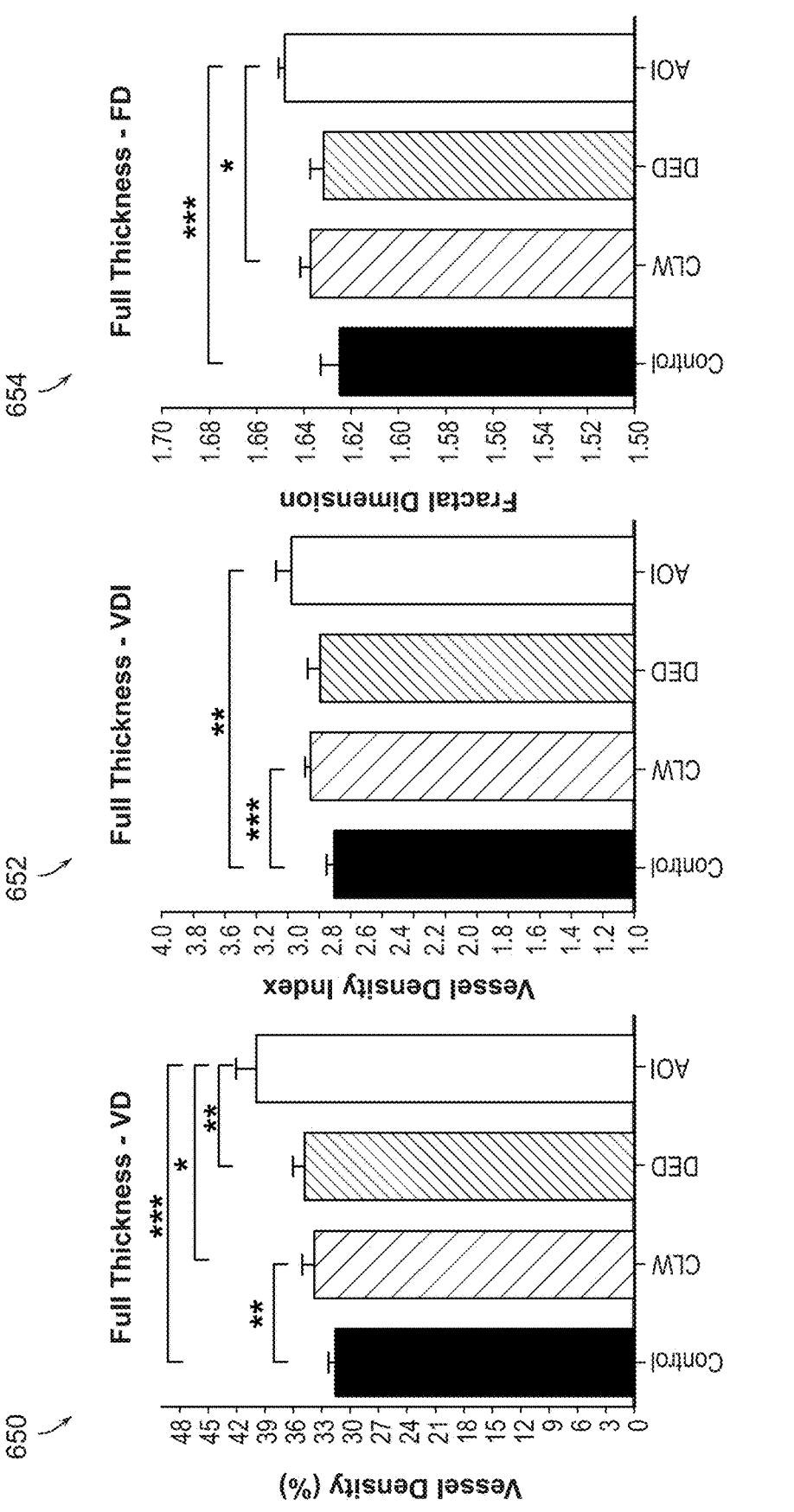
Figure 6F:
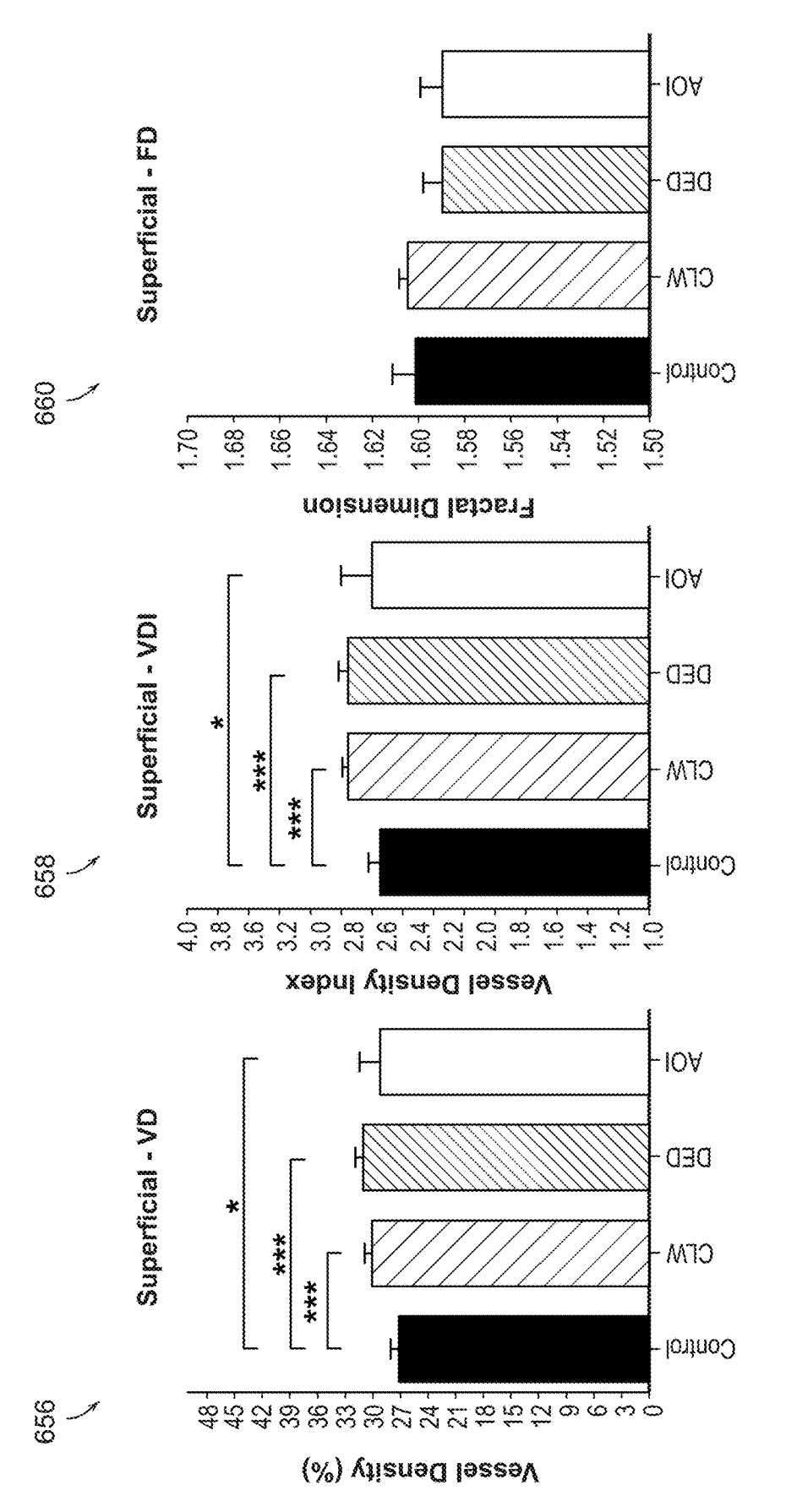
Figure 6F:
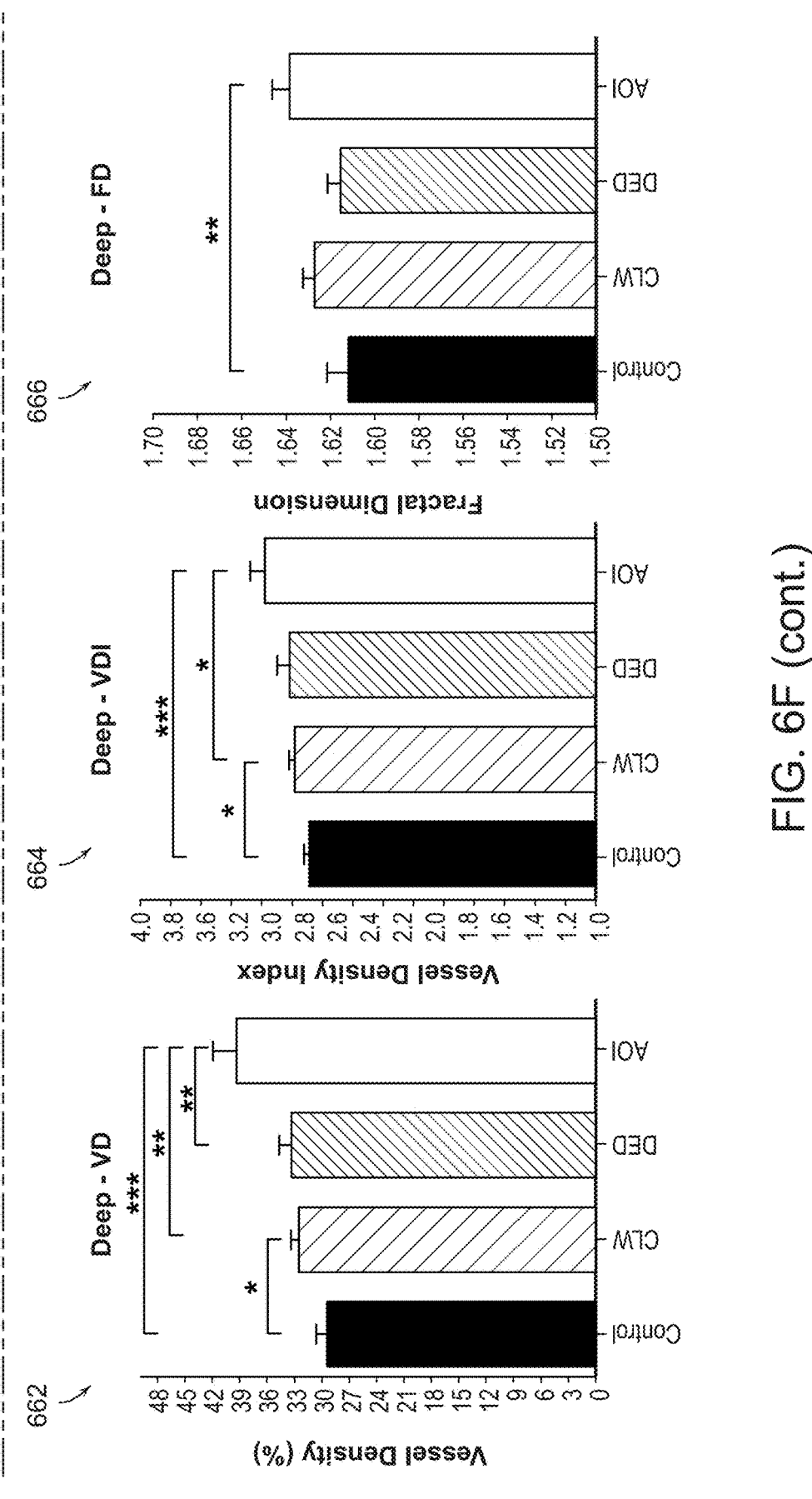

FIG. 6F includes graphs demonstrating the vessel density (VD), vessel diameter index (VDI) and fractal dimension (FD) distribution between the control, contact lens wearer (CLW), dry eye disease (DED) and acute ocular inflammation (AOI) groups. The top row includes the graphs 650, 652, and 654, corresponding to full thickness layer experimental data. The middle row includes the graphs 656, 658, and 660 corresponding to the superficial layer. And the bottom row includes the graphs 662, 664, and 666 corresponding to the deep layer. Bars in the various graphs marked with a single asterisk ('*') have a p<0.050, bars marked with two asterisks ('') have a p≤0.010, and bars with three asterisks ('*') have a p≤0.001.

As noted, the determination of ocular redness grading scales based on blood vessel characteristics determined through a non-invasive AS-OCTA imaging procedure of the ocular surface provides an objective measure of a level of inflammation of a patient's eye. This objective measure can facilitate and improve accuracy of diagnosing various medical conditions or ailments (such as dry eye syndrome), determine efficacy of treatment procedures (e.g., through use of objective measures to determine an increase or decrease in inflammation levels), identify subjects for studies, etc. The ocular redness grading scale derived using the methods and implementations described herein provide an important parameter to evaluate the response to treatment and adverse effects of drugs in clinical trials, which can include eye drops or systemic drugs.

Thus, in some embodiments, procedures for determining the efficacy of a treatment for eye inflammation (e.g., treatment for dry eye syndrome or limbal stem cell insufficiency) in a subject is disclosed. Such procedures include determining at a first and second time points, levels of inflammation (e.g., based on blood vessel characteristics determined from OCT-based image data for ocular surface of the patient's eye, or based on other types of measurements), and comparing the level of eye inflammation determined at the first and second time points, where the first time point is prior to treatment and the second time point is any time point following the initiation of treatment (or, alternatively, the first time point may be following the initiation of treatment, and the second time point may be at a later time point during or after treatment). In situations where the ocular redness grading scales for the subject are determined not to have changed (or the extent of the changes is less than some threshold amount or percentage), it can be inferred that the treatment administered was ineffective and did not substantially ameliorate the inflammation levels determined at the first time point.

Alternatively, in some embodiments, upon determination that for a subject for whom there has not substantial reduction in the grading scales used to quantify the level of inflammation at a second time instance (after application of a treatment following a determination of an ocular redness grading scale that indicated a particular inflammation level), an inference can be made that that the treatment was not effective in the subject. In some embodiments, where the treatment has been indicated to be ineffective on the subject, the procedure to determine the efficacy of a treatment can further include administering, recommending, or prescribing an alternate treatment to the subject. The alternate treatment can be a different therapeutic agent or a different combination of one or more therapeutic agents. The alternate treatment can be an increased dosage of one or more therapeutic agents currently being taken by the subject, an increase in the frequency of administration of one or more therapeutic agents currently being taken by the subject, or an alteration in the route of delivery of one or more therapeutic agents being currently taken by the subject. Some embodiments further include recording the results of these methods in the subject's medical records (e.g., recording the results in a computer readable medium), performing a diagnostic test for eye inflammation (e.g., dry eye syndrome, limbal stem cell deficiency, allergy, or graft versus host disease) on one or more lineal family members of the subject using the methods and procedures described herein, or monitoring one or more lineal family members of the subject diagnosed (using the methods described herein) for the development of eye inflammation (e.g., the development of dry eye syndrome, limbal stem cell deficiency, allergy, or graft versus host disease) (e.g., using any of the methods described herein).

It should be noted that the efficacy of a treatment can be independently evaluated based on other procedures that can be used to assess the level of inflammation in a subject. For example, and as described in U.S. 2013/0336557, entitled "Inflammatory Eye Disorders," an assessment of whether a particular treatment is effective can further be based on whether the subject has one or more (e.g., two, three, four, five, six, seven, eight, or nine) of an elevation or no substantial change in the number or percentage of hyperreflective superficial epithelial cells present in the cornea (e.g., in the center of the cornea), an elevation or no substantial change in the average size of superficial epithelial cells present in the cornea (e.g., in the center of the cornea), a decrease or no substantial change in the density of superficial epithelial cells present in the cornea (e.g., in the center of the cornea), an elevation or no substantial change in the density of dendritic immune cells present in the cornea (e.g., in the center of the cornea), an elevation or no substantial change in the average size of dendritic immune cells present in the cornea (e.g., in the center of the cornea), and an elevation in the average area covered by dendritic immune cells present in the cornea (e.g., in the center of the cornea), a decrease or no substantial change in the density or average length of nerves present in the cornea, a decrease or no substantial change in the amount of branching in nerves present in the cornea, and a decrease or no substantial change in the total number of nerves present in the cornea, determined at the second time point compared to the first time point, indicates that the treatment was not effective in the subject. In such embodiments, these independent determinations of the inflammation level of the subject can be combined with the results obtained via the OCT-based determination of ocular redness grading scales. That is, a treatment may be deemed to be ineffective if one or more of the various indicators of no reduction in inflammation level (with one of those indicators being that the OCT-based determination of ocular redness grading scale at a second time instance did not change, or did not significantly change, following administration of a treatment subsequent to a grading scale determination at a first time instance) are present. The actual number of indicators that lead to a conclusion that a treatment is ineffective can also be used to assign an effectiveness score to the treatment used (e.g., if there was an improvement in the condition of the eye, or some other body part, in relation to one criterion, but no improvement in relation to the other criteria, this would result in an effectiveness score of, for example 1 on a scale of 10).

In some examples, the above procedures and methods to assess efficiency of a treatment can be performed by a medical professional (e.g., a physician, a physician's assistant, a nurse, a nurse's assistant, or a laboratory technician). The subject can be first diagnosed as having eye inflammation (e.g., diagnosed as having dry eye syndrome, limbal stem cell insufficiency, graft versus host disease, or allergy), or has an increased risk of developing eye inflammation (e.g., increased risk of developing dry eye syndrome, limbal stem cell insufficiency, or graft versus host disease, allergy) or is suspected of having eye inflammation. It is to be noted that the subject may show one or more symptoms of eye inflammation. In some embodiments, the subject does not present with a symptom of eye inflammation that can be observed without the use of an OCT-based imaging apparatus, a microscope, or some other assessment apparatus. In some examples, the subject may have a form of eye inflammation (e.g., a form of dry eye syndrome, limbal stem cell insufficiency, graft versus host disease, or allergy) that is refractory to previous therapeutic treatment. In some embodiments, the subject has had eye inflammation for at least one week (e.g., at least two weeks, three weeks, one month, two months, three months, four months, six months, or one year). In some situations, the eye inflammation (e.g., dry eye syndrome) may have been caused by an autoimmune condition (e.g., any of the autoimmune conditions described herein).

In some embodiments, the subject may be a child, a teenager, or an adult (e.g., at least 18, 20, 25, 30, 35, 40, 45, 50, 55, 60, 65, 70, 75, 80, or 90 years old). The subject may be male or female (e.g., a post-menopausal female). In some embodiments, the subject may already be receiving a treatment for eye inflammation (e.g., a treatment for dry eye syndrome, limbal stem cell insufficiency, graft versus host disease, or allergy), in which case the subject may terminate the previous treatment for eye inflammation, and the efficacy of a new treatment is determined using the methods described herein. In some situations, the subject is already receiving a treatment for eye inflammation, but begins to take one or more additional (new) therapeutic agent(s) in combination with the old treatment, and the efficacy of the combination of the one or more additional (new) therapeutic agents and the old treatment are determined using the procedures and methods described herein. In some situations, the subject may already be receiving one or more therapeutic agent(s) for eye inflammation and the efficacy of an increased dosage and/or an increased frequency of dosing of the previously administered one or more therapeutic agent(s) is determined using the procedures and implementations described herein. In some embodiments, the subject is already receiving one or more therapeutic agent(s) for eye inflammation, and the efficacy of an alternative route of administration of the one or more therapeutic agent(s) previously administered to the subject is determined using the methods and procedures described above.

The amount of time between the first and the second time point can be at least one week (e.g., at least two weeks, three weeks, one month, two months, three months, four months, six months, or one year), or any other period of time (e.g., days, hours, or minutes). Some embodiments further include administering a treatment (e.g., one or more therapeutic agents) to the subject between the first and second time points/instances. In some examples, the procedures to gauge the efficacy of treatment may further include administering a treatment to the subject prior to the first time point. Some embodiments further include determining one or more indicators of inflammation (e.g., ocular redness grading scale determined based on blood vessel characteristics derived from OCT-based imaging, number or percentage of hyperreflective superficial epithelial cells present in the cornea, average size of superficial epithelial cells present in the cornea, and other of the indicators described herein) at one or more additional time points (e.g., after the second time point) in the eye of the subject having eye inflammation. In some variations, the one or more additional time points occur after the end of the therapeutic treatment.

Some of the implementations described herein to determine ocular redness grading scales (indicative of level of eye inflammation) may be used in the course of performing procedures/methods to treat a subject. Thus, provided are methods of treating a subject having eye inflammation that include selectively administering to an eye(s) of a subject having eye inflammation and determined to have, for example, an ocular redness grading scale value exceeding some pre-determined reference level, a therapeutic agent such as a topical steroid solution. Alternatively, the method may include selectively orally or topically administering to a subject having eye inflammation and at least two immunosuppressive agents (e.g., at least one steroid). Some embodiments may further include one or more of: deriving an ocular redness grading scale (e.g., according to some of the implementations described herein), comparing the derived ocular redness grading scale to a reference level, and selecting a subject that has an elevated ocular redness grading scale value/level (as compared to the reference level) for treatment. In some embodiments, the procedure to treat the subject may further include selecting a subject having eye inflammation (e.g., a subject having dry eye syndrome, limbal stem cell insufficiency, graft versus host disease, or allergy). It should be noted that in some implementations, determining whether the subject has eye inflammation may further be based on determining additional indicators of eye inflammation, e.g., indicators determined through performance of an in vivo confocal microscopy.

The methods/procedures for treating a subject may be performed by a medical professional (e.g., a physician, a physician's assistant, a nurse, a nurse's assistant, or a laboratory technician). The subject may already be taking one or more pharmaceutical agents for treatment of eye inflammation, and the subject may be instructed or advised to discontinue taking one or more of the previously prescribed one or more pharmaceutical agents. In some embodiments, the subject may already be taking one or more pharmaceutical agents for treatment of eye inflammation, and the topical steroid solution or the topically- or orally-administered at least two (e.g., three or four) immunosuppressive agents is administered to the subject in combination with the one or more pharmaceutical agents previously taken by the subject.

The reference level against which the ocular redness grading scale is compared can be a threshold level or can be a pre-determined ocular redness grading scale for a healthy subject (e.g., a subject that does not have an eye disorder, or does not have one or more symptoms of an eye disorder, or a subject that has not been diagnosed as having an eye disorder).

A topical steroid solution selected to be administered to a subject determined to have eye inflammation (e.g., based on the implementations described herein) may contain one or more (e.g., two, three, or four) steroid(s) selected from the group of loteprednol etabonate, cortisone, dexamethasone, hydrocortisone, prednisolone, prednisone, methylprednisolone, betamethasone, dexamethasone, rimexolone, prednisolone acetate, triamcinolone, beclometasone, fludrocortisone, deoxycorticosterone, aldosterone, betamethasone, deoxycorticosterone, and aldosterone. The topical steroid solution may include loteprednol etabonate. In some examples, the topical steroid solution may include 1% or 0.12% prednisolone acetate. Other types of topical steroid solutions may be used. The topical steroid solution may be administered to an eye of the subject at least once a day (e.g., at least twice, three times, or four times a day). The administration of the topical steroid solution can occur before bedtime and/or shortly after awakening (e.g., within one hour of awakening) in the morning.

The at least two immunosuppressive agents that are topically administered are selected from the group of antibodies (e.g., fully human or humanized antibodies) that specifically bind to CD20, CD25 (e.g., basiliximab or daclizumab), or CD3 (e.g., muromonab), calcineurin inhibitors (e.g., ciclosporin, pimecrolimus, tacrolimus, sirolimus, and/or cyclosporine) interferons (e.g., interferon-$\beta$; steroids (e.g., any of the steroids known in the art or described herein); interleukin-1 receptor antagonists, myophenolate mofetil, Prograph®, azathioprine, methotrexate, and/or TNF-$\alpha$ binding proteins (e.g., antibodies and/or soluble TNF-$\alpha$ receptors, e.g., infliximab, etanercept, and/or adalimumab). Additional types of immunosuppressive agents that can be topically administered may also be used. In some embodiments, the at least one of the at least two immunosuppressive agents is a steroid (e.g., one or more of loteprednol etabonate, cortisone, dexamethasone, hydrocortisone, prednisolone, prednisone, methylprednisolone, betamethasone, dexamethasone, triamcinolone, beclometasone, fludrocortisone, deoxycorticosterone, aldosterone, betamethasone, deoxycorticosterone, and/or aldosterone). At least one of the at least two immunosuppressive agents is a steroid and at least one of the at least two immunosuppressive agents is selected from pimecrolimus, tacrolimus, sirolimus, and cyclosporine. Additional examples of immunosuppressive agents that can be used in the presently described methods and procedures are known in the art.

The at least two (e.g., three or four) immunosuppressive agents may be topically and/or orally administered to an eye of the subject at least twice a week (e.g., at least twice, three times, or four times a day). In some examples, the topical and/or oral administration of the at least two immunosuppressive agents occurs before bedtime and/or shortly after awakening (e.g., within one hour of awakening) in the morning. The at least two immunosuppressive agents may be formulated together (e.g., present in the same liquid formulation for optical administration). In some embodiments, the at least two immunosuppressive agents are formulated as separate compositions (e.g., each formulated in separate liquid formulations for optical administration).

Also provided are methods of treating a subject (e.g., a subject having eye inflammation, e.g., a subject having dry eye syndrome, acute allergy, chronic allergy, limbal stem cell insufficiency, or graft versus host disease, or any of the other inflammatory eye diseases/disorders described herein) that include selectively orally or topically administering to a subject, determined to have an elevated number of ocular redness grading scale as compared to a corresponding reference value (and/or to have other ocular parameter indicating, in comparison to respective reference levels, eye inflammation), at least one anti-inflammatory steroid and/or at least one (e.g., two, three, or four) immunosuppressive agent (e.g., at least one calcineurin inhibitor).

As noted, the procedures/methods for treating the subject may be based, jointly or separately, on determining other types of indicators of eye inflammation, e.g., determining the level of the number or average density of dendritic inflammatory cells present in the peripheral cornea. Thus, in such embodiments, the methods/procedures for treating a subject may further include one or more of: determining one or more other indicators of eye inflammation (e.g., determining level of the number or average density of dendritic inflammatory cells present in the peripheral cornea), comparing the determined level of the one or more other eye inflammation indicators to respective reference levels, and/ or selecting a subject having an elevated number of the one or more eye inflammation indicators as compared to the reference level for treatment. As noted, the one or more other eye inflammation indicators may be determined using in vivo confocal microscopy implementations. Some embodiments further include selecting a subject having an inflammatory eye disease (e.g., dry eye syndrome, acute allergy, chronic allergy, or any of the other inflammatory eye diseases described herein).

In some embodiments, the at least one anti-inflammatory steroid used to treat a subject determined, or deemed, to have eye inflammation (whether based on ocular redness grading scale measure, or some other type of determined indicator) is selected from the group of: hydrocortisone, cortisone, prednisone, prednisolone, methylprednisolone, dexamethasone, betamethasone, triamcinolone, beclometasone, fludrocortisone, deoxycorticosterone, and aldosterone. Additional examples of anti-inflammatory steroids known in the art may be used. In some embodiments, the at least one anti-inflammatory steroid is administered to an eye of the subject at least once a day (e.g., at least twice, three times, four times a day). In some embodiments, the at least one anti-inflammatory steroid is orally administered to the subject at least once a week (e.g., at least twice a week or at least once a day). In some embodiments, the at least one anti-inflammatory steroid occurs before bedtime and/or shortly after awakening (e.g., within one hour of awakening) in the morning. In some embodiments, the at least one anti-inflammatory steroid and the at least one immunosuppressive agent (e.g., a calcineurin inhibitor) are administered at approximately the same time (e.g., within 10 minutes of each other).

In some embodiments, the at least one immunosuppressive agent is a calcineurin inhibitor (e.g., ciclosporin, pimecrolimus, tacrolimus, sirolimus, or cyclosporine). Additional examples of immunosuppressive agents that can be used in the methods described herein are known in the art and are described herein (e.g., any of the immunosuppressive agents described herein). In some embodiments, the at least one anti-inflammatory agent and the at least one immunosuppressive agent may be present in the same formulation (e.g., a pharmaceutically acceptable solution for optical administration or a solid formulation (e.g., a pill or capsule) for oral administration).

Also provided are methods of selecting a subject (e.g., a subject having eye inflammation, e.g., dry eye syndrome, acute allergy, chronic allergy, limbal stem cell insufficiency, or graft versus host disease), based, in part, on a determined ocular redness grading scale derived from blood vessel characteristics and/or on other ocular parameters, for participation in a clinical study. These methods include determining a level of one or more (e.g., 2, 3, 4, 5, 6, 7, 8, 9, 10, 11, 12, 13, 14, 15, 16, 17, 18, 19, or 20) of the following ocular physical parameters: (i) the density of dendritic immune cells present in the cornea (e.g., in the center of the cornea), (ii) the average size of dendritic immune cells present in the cornea (e.g., in the center of the cornea), (iii) the average area covered by dendritic immune cells present in the cornea (e.g., in the center of the cornea), (iv) the number or average density of dendritic inflammatory cells present in the peripheral cornea, (v) the hyperreflectivity of epithelial cells in the conjunctiva, (vi) the dendritic cell density in the conjunctiva, (vii) the average dendritic cell size in the conjunctiva, (viii) the number of hyperreflective dendritic cells in the conjunctiva, (ix) the dilation of the lumen of blood vessels in the conjunctiva, (x) the average size of inflammatory cells in the blood vessels in the conjunctiva, (xi) the sticking (the average time of transitory residence) of inflammatory cells to the blood vessels walls in the conjunctiva, (xii) the average size of inflammatory cells in the lymph vessels in the conjunctiva, (xiii) the number of inflammatory cells present in the lymph vessels of the conjunctiva, and/or (xiv) an ocular redness grading scale derived from blood vessel characteristics determined from OCT-based imaging of the ocular surface; comparing the one or more of (i)-(xiv) (listed above) determined in the eye of the subject to one or more corresponding reference values; and selecting a subject having one or more of, for example: an elevation in the density of dendritic immune cells present in the cornea (e.g., in the center of the cornea), an elevation in the average size of dendritic immune cells present in the cornea (e.g., in the center of the cornea), an elevation in the average area covered by dendritic immune cells present in the cornea (e.g., in the center of the cornea), an elevation in the number or average density of dendritic inflammatory cells present in the peripheral cornea, an elevation in dendritic cell density in the conjunctiva, an elevation in the average dendritic cell size in the conjunctiva, an elevation in the number of hyperreflective dendritic cells in the conjunctiva, an elevation in the dilation of the lumen of blood vessels in the conjunctiva, an elevation in the average size of inflammatory cells in the blood vessels in the conjunctiva, an elevation in the sticking (elevation in the average time of transitory residence) of inflammatory cells to the blood vessels walls in the conjunctiva, an elevation in the average size of inflammatory cells in the lymph vessels in the conjunctiva, an elevation in the number of inflammatory cells present in the lymph vessels of the conjunctiva, and/or an elevated ocular redness grading scale measure, as compared to the one or more corresponding reference values for participation in a clinical study. In some embodiments, the determining is performed using in vivo confocal microscopy and/or AS-OCTA imaging implementation.

Alternatively, in the above methods, a subject having one or more of a decrease or no substantial change in the density of, for example, dendritic immune cells present in the cornea (e.g., in the center of the cornea), a decrease or no substantial change in the average size of dendritic immune cells present in the cornea (e.g., in the center of the cornea), a decrease or no substantial change in the average area covered by dendritic immune cells present in the cornea (e.g., in the center of the cornea), a decrease or no substantial change in the number or average density of dendritic inflammatory cells present in the peripheral cornea, a decrease or no substantial change in the hyperreflectivity of epithelial cells in the conjunctiva, a decrease or no substantial change in dendritic cell density in the conjunctiva, a decrease or no substantial change in the average dendritic cell size in the conjunctiva, a decrease or no substantial change in the number of hyperreflective dendritic cells in the conjunctiva, a decrease or no substantial change in the dilation of the lumen of blood vessels in the conjunctiva, a decrease or no substantial change in the average size of inflammatory cells in the blood vessels in the conjunctiva, a decrease or no substantial change in the sticking (a decrease or no substantial change in the average time of transitory residence) of inflammatory cells to the blood vessels walls in the conjunctiva, a decrease or no substantial change in the average size of inflammatory cells in the lymph vessels in the conjunctiva, a decrease or no substantial change in the number of inflammatory cells present in the lymph vessels of the conjunctiva, a decrease or no substantial change in the ocular redness grading scale, as compared to the one or more corresponding reference values is selected for participation in a clinical study (e.g., selected as a control subject).

Also provided are methods of selecting a subject for participation in a clinical study that include: determining a level of one or more of the following ocular physical parameters: (i) the density of dendritic immune cells present in the cornea (e.g., in the center of the cornea), (ii) the average size of dendritic immune cells present in the cornea (e.g., in the center of the cornea), (iii) the average area covered by dendritic immune cells present in the cornea (e.g., in the center of the cornea), and/or the ocular redness grading scale as derived from blood vessel characteristics (determined from blood flow image data obtained using AS-OCTA imaging) in the ocular surface (other physical parameters may also be used); comparing the above ocular physical parameters to respective reference values; and selecting a subject, for participation in a clinical study, having one or more of, for example, an elevation in the density of dendritic immune cells present in the cornea (e.g., in the center of the cornea), an elevation in the average size of dendritic immune cells present in the cornea (e.g., in the center of the cornea), an elevation in the average area covered by dendritic immune cells present in the cornea (e.g., in the center of the cornea), and/or an elevation of the ocular redness grading scale measure, as compared to the one or more corresponding reference values. In some embodiments, the determining is performed using in vivo confocal microscopy, and/or based on an AS-OCTA imaging of the ocular surface.

In some embodiments, a grading scale may be used as a tool to quantify the severity of a condition based on a set of standardized descriptions or illustrations. In conventional ocular redness grading scales, Grade 0 often refers to a condition of 'absent' redness or 'normal', Grade 1 as 'trace' 'slight' or 'very slight', Grade 2 as 'mild' or 'slight', Grade 3 as 'moderate' and Grade 4 generally describes 'severe' ocular redness condition. However, these scales were constructed independently and agreement between scales is not necessarily identical, with different ranges of severity depicted in the same group or grade. Due to lack of validation, or objectivity or general acceptance of the scales, these illustrative grading scales have not been fully implemented into clinical practice and specially research. Another disadvantage of the previous scales is the large incremental change between grades as opposed to a continuous grading scale that provides a more sensitive measure.

The method may also include selecting one or more control subjects for the clinical study, that are determined to have one or more of, for example, a decrease or no substantial change in the density of dendritic immune cells present in the cornea (e.g., in the center of the cornea), a decrease or no substantial change in the average size of dendritic immune cells present in the cornea (e.g., in the center of the cornea), a decrease or no substantial change in the average area covered by dendritic immune cells present in the cornea (e.g., in the center of the cornea), and/or a decrease or no substantial change of the ocular redness grading scale, as compared to the one or more corresponding reference values.

Figure 7:
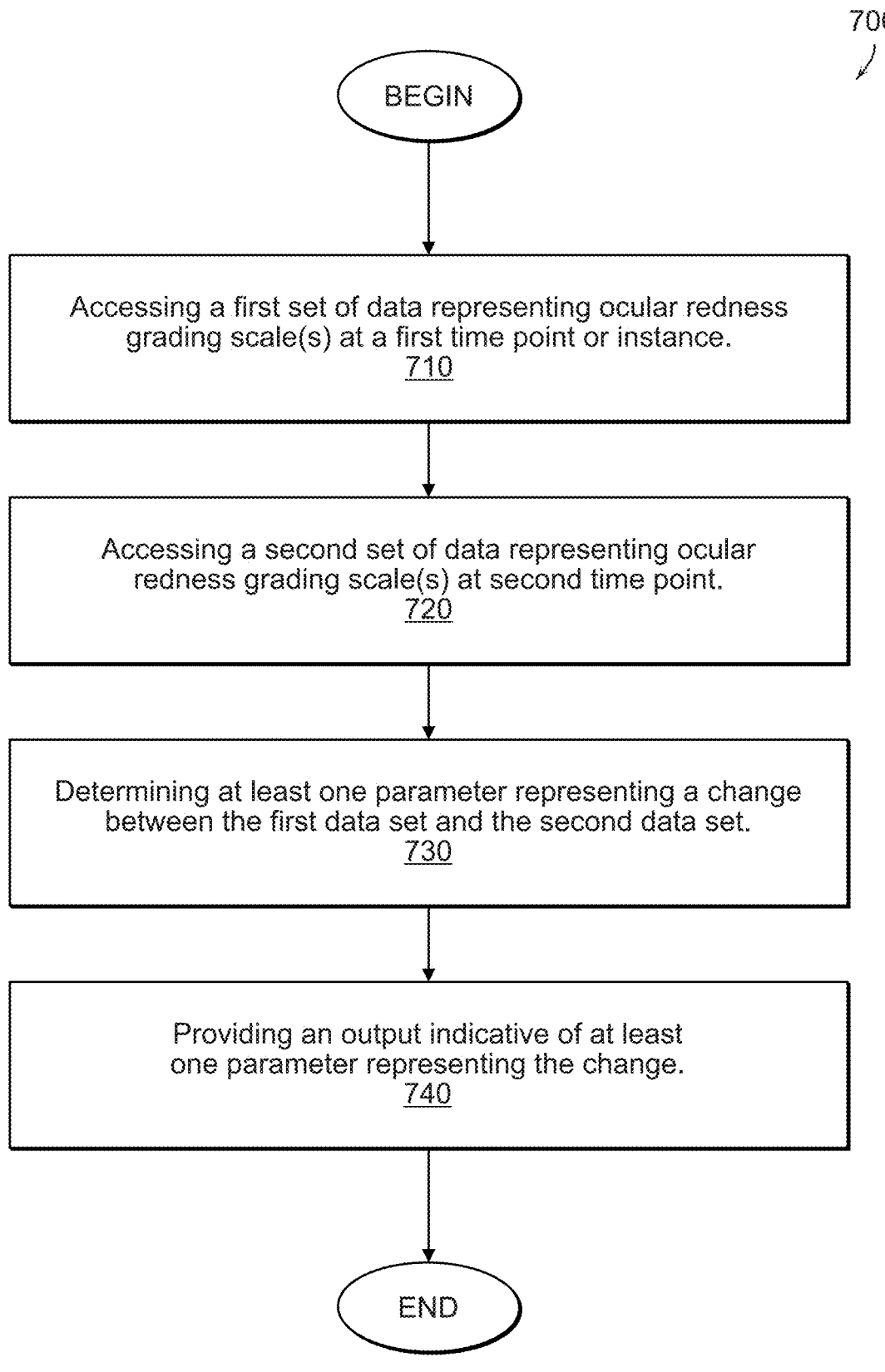
FIG. 7 is a flowchart of an example procedure to evaluate a change in an eye condition of a subject.

FIG. 7 depicts a flowchart of an example procedure 700 to evaluate a change in eye condition of a subject. The operations illustrated in FIG. 7 may be used to facilitate performing the various methods/procedures described herein, including, for example, to determine the efficacy of a therapy to alleviate eye inflammation, selecting subjects for studies of therapies to alleviate or treat eye inflammation, etc. The operations depicted in the flowchart 700 can be performed, for example, by a controller or computing device such as the computing-based device 300 of FIG. 3, or the device 154 depicted in FIG. 1, a processing unit such as the unit 152 (which may comprise part of the computing-based device 154), or any other controller device in communication with the system 100 of FIG. 1.

The procedure 700 includes accessing 710 a first set of data representing ocular redness grading scale(s) at a first time point or instance. In some embodiments, accessing the first set of data may include obtaining data representing blood flow characteristics at the ocular surface of an eye of the patient (such data may be in the form of AS-OCTA image data acquired, at about the time of the first time point or at an earlier time point, using an imaging apparatus such as the one shown in FIG. 1), and determining from the data so obtained characteristics of blood vessels at the ocular surface. The ocular redness grading scale(s) can then be derived from the determined blood vessel characteristics. The image data used to derive the ocular redness grading scale may be obtained per anatomical layer of the ocular surface, or per some convenient depth benchmark layer (full thickness, superficial layer, deep layer). Obtaining the blood flow data, determining blood vessel characteristics therefrom, and deriving the ocular redness grading scale may be performed in a manner similar to that described in relation to FIGS. 1 and 2. Alternatively, the first set of data may be acquired using confocal microscopy (as described herein). The first-time point may be, for example, a time instance that occurred before commencing treatment of the eye.

The procedure 700 further includes accessing 720 a second set of data representing ocular redness grading scale(s) at a second-time point/instance. Here too, accessing the second set of data may include obtaining data flow characteristics for the ocular surface (obtained through AS-OCTA imaging of the ocular surface of the eye), determining blood vessel characteristics image of the eye, and deriving the ocular redness grading scales. The second-time point/instance associated with the second set of data may correspond to a time point after the treatment has been administered for a finite length of time. In some implementations, the first-time point may be a time point following the initiation of the treatment, and the second time point may be a later time point during or after the treatment. In some implementations, the first and/or the second set of data can also represent one or more reference values associated with evaluating eye conditions. For example, the second set of data can include values representing threshold conditions for diagnosing dry eye syndrome, or for determining if the subject can be included in a clinical study.

With continued reference to FIG. 7, the procedure 700 further includes determining 730 at least one parameter representing a change between the data sets. For example, the parameter may represent the change in the condition of the eye between the first and second time points. Determining the parameter can include computing the relative change (as a percentage) of the ocular redness grading scale between the first and second time points. As noted, in some embodiments, other ocular parameters that indicate inflammation levels of the eye may be computed. Some examples of changes, between the first and second time points, in the levels/values of some such ocular parameters, which may be considered with the ocular redness grading scales to evaluate clinical studies relating to treatments for inflammatory eye disorders, include, (i) a density of dendritic immune cells present in the cornea, (ii) the average size of dendritic immune cells present in the cornea, (iii) the average area covered by dendritic immune cells present in the cornea, ocular redness grading scales, etc. In some implementations, determining the parameter includes calculating the number of, or average density of dendritic inflammatory cells present either in the central or the peripheral portion of the cornea. By comparing the number of, or average density of dendritic inflammatory cells present in the cornea between images taken at two time points, a change in the condition of the eye between the two time points can be determined. In some implementations, the number of, or average density of dendritic inflammatory cells present in the cornea can be compared to a reference value (e.g., the number or average, respectively, of an individual considered to have a healthy eye) for purposes such as diagnosis, or screening subjects for inclusion in a clinical study. The extent of change between the two time points with respect to other ocular parameters can similarly be computed.

The procedure 700 additionally includes providing 740 an output indicative of the at least one parameter representative of change between the two data sets. The output can be provided, for example, by displaying a representation of the output on a display device, or storing data representing the output on a computer-readable non-transitory storage device. The output can identify one or more conditions of the eye based on the determined parameter. For example, the output can identify dry eye syndrome in the subject based on one or more of a number/value of the ocular redness grading scale, a determined elevation in the ocular redness grading scale of a subject relative to a pre-determined value for one or more healthy subjects, number or percentage of hyper-reflective superficial epithelial cells present in the cornea, an elevation in the average size of superficial epithelial cells present in the cornea, a decrease in the density of superficial epithelial cells present in the cornea, an elevation in the density of dendritic immune cells present in the cornea, an elevation in the average size of dendritic immune cells present in the cornea, an elevation in the average area covered by dendritic immune cells present in the cornea.

Embodiments of a method for therapeutic monitoring can be implemented according to the procedure 700 of FIG. 7. For example, the operations at 710 of accessing the first set of data may include obtaining, at a first time instance, a first set of data representing a first ocular grading scale, with such obtaining including determining first blood flow characteristics at an ocular surface of an eye of a patient, determining first characteristics of blood vessels at the ocular surface of the eye based on the determined first blood flow characteristics, and deriving the first ocular grading scale based on the determined first characteristics of the blood vessels at the ocular surface of the eye. In the example embodiments of the therapeutic monitoring method, the operations at 720 of FIG. 7 of accessing the second set of data may further include obtaining, at a second time instance, a second set of data representing a second ocular grading scale, including determining second blood flow characteristics at the ocular surface of the eye of the patient, determining second characteristics of blood vessels at the ocular surface of the eye based on the determined second blood flow characteristics, and deriving the second ocular grading scale based on the determined second characteristics of the blood vessels at the ocular surface of the eye.

The operations 730 of determining at least one parameter may thus include determining at least one parameter representing a change between the first set of data and the second set of data. Determining the at least one parameter representing the change between the first set of data and the second set of data may include computing a percentage change between the second ocular grading scale and the first ocular grading scale.

Optionally, in some examples, embodiments of the therapeutic monitoring method may include the operations of 740 (depicted in FIG. 7) of providing an output indicative of the at least one parameter representing the change. For example, the therapeutic monitoring method may further include providing an output indicative of the at least one parameter representing the change between the first set of data and the second set of data.

In some examples, the therapeutic monitoring method may additionally include administering to the patient a selected therapeutic medication following the obtaining of the first set of data such that the second blood vessel characteristics are determined in response to the selected therapeutic medication administered to the patient. Examples of therapeutic medications can include an anti-inflammatory steroid and/or an immunosuppressive agent. The therapeutic monitoring method can allow, for example, to determine the efficacy of the medication being administered. Thus, in such situations, the determined at least one parameter representing the change between the first set of data and the second set of data may be representative, at least in part, of an effect of the selected therapeutic medication on changes to ocular redness level in the eye of the patient. More particularly, in some examples, the therapeutic monitoring method may further include determining efficacy of the selected therapeutic medication, or an existence of an adverse event (AE) or a serious adverse event (SAE), based on the determined at least one parameter representing the change between the first set of data and the second set of data after administering the selected therapeutic medication.

In some embodiments, the therapeutic monitoring method (implemented according to the framework of FIG. 7) can be used to screen individuals for clinical studies and trials. Thus, in such embodiments, the therapeutic monitoring method may further include selecting the patient from a pool of candidate subjects available to test efficacy of the selected therapeutic medication. Selecting the patient can include subsequent to obtaining the first set of data, determining that the patient potentially suffers from a particular medical condition based on a comparison of the first ocular grading scale derived for the patient to a reference value. On the other hand, another candidate subject from the pool may be excluded from receiving the selected therapeutic medication (e.g., excluded from the clinical trial or study) in response to a determination, based on another comparison of a respective other first ocular grading scale derived for the other candidate to the reference value, that the other candidate subject likely does not suffer from the particular medical condition.

In some embodiments, the therapeutic monitoring method can be used to identify the existence of a medical condition affecting an individual, determine the severity of such a medical condition (or determine the severity of a medical condition that the individual is otherwise known to suffer from, i.e., independently of any determination based on ocular redness levels computed according to the imaging approaches described herein), and/or determine responsiveness of the individual to a therapy administered to the individual to treat the medical condition. In such embodiments, the methodology of FIG. 7 can be used to compare a baseline (first measurement) to subsequent measurements to differentiate levels of inflammation to ascertain treatment decisions. Baseline measurement will establish if a patient needs treatment. A second, third, and/or subsequent measurements (serving as "biomarkers") will determine response to therapy. The implementation of the methodology of FIG. 7 can also be used to sub-stratify patient population based on response to therapy (e.g., stratify the subject population into groups of responders, non-responders, intermediate responders, and/or other group classifications). Thus, some embodiments of the therapeutic monitoring method can further include determining one or more of a medical condition or a severity of the medical condition, of the patient, based, at least in part, on at least the first ocular grading scale. Embodiments can further include determining a medication with an associated dosage for treating the medical condition or the severity of the medical condition, and administering the medication at the associated dosage. Some additional embodiments can further include determining, subsequent to administering the medication at the associated dosage, whether to adjust one or more of the medication or the associated dosage for the medication based on the at least one parameter representing the change between the first set of data and the second set of data. Additional embodiments can further include determining at subsequent time instances, subsequent to administering the medication at the associated dosage, based on subsequently obtained sets of data, a level of responsiveness of the patient to the medication at the associated dosage, with the subsequent time instances including at least the second time instance, and with the subsequent sets of data including at least the second set of data. In some examples, the therapeutic monitoring method may also include providing an output indicative of the level of responsiveness of the patient to the medication at the associated dosage.

In some embodiments, obtaining the first set of data and obtaining the second set of data (e.g., through implementations of the operations 710 and 720 of FIG. 7) can include determining at the first time instance and at the second time instance one or more of, for example, (i) density of dendritic immune cells present in a cornea of the eye of the patient, (ii) average size of the dendritic immune cells present in the cornea of the eye of the patient, (iii) average area covered by the dendritic immune cells present in the cornea of the eye of the patient, (iv) number or average density of dendritic inflammatory cells present in a peripheral cornea of the eye of the patient, (v) a hyperreflectivity of epithelial cells in a conjunctiva of the eye of the patient, (vi) dendritic cell density in the conjunctiva of the eye of the patient, (vii) average dendritic cell size in the conjunctiva of the eye of the patient, (viii) number of hyperreflective dendritic cells in the conjunctiva of the eye of the patient, (ix) dilation of lumen of blood vessels in the conjunctiva of the eye of the patient, (x) average size of inflammatory cells in the blood vessels in the conjunctiva of the eye of the patient, (xi) a sticking value, representative of an average time of transitory residence of inflammatory cells to the blood vessels walls in the conjunctiva of the eye of the patient, (xii) average size of inflammatory cells in the lymph vessels in the conjunctiva of the eye of the patient, and/or (xiii) a number of inflammatory cells present in the lymph vessels of the conjunctiva of the eye of the patient. In such embodiments, determining (e.g., via the operations 730 of FIG. 7) the at least one parameter representing the change between the first set of data and the second set of data may further include determining level of change between the first time instance and the second time instance of one or more of, for example, (i) a change in the density of dendritic immune cells present in a cornea of the eye of the patient, (ii) a change in the average size of the dendritic immune cells present in the cornea of the eye of the patient, (iii) a change in the average area covered by the dendritic immune cells present in the cornea of the eye of the patient, (iv) a change in the number or average density of dendritic inflammatory cells present in a peripheral cornea of the eye of the patient, (v) a change in the hyperreflectivity of epithelial cells in a conjunctiva of the eye of the patient, (vi) a change in the dendritic cell density in the conjunctiva of the eye of the patient, (vii) a change in the average dendritic cell size in the conjunctiva of the eye of the patient, (viii) a change in the number of hyperreflective dendritic cells in the conjunctiva of the eye of the patient, (ix) a change in dilation of lumen of blood vessels in the conjunctiva of the eye of the patient, (x) a change in the average size of inflammatory cells in the blood vessels in the conjunctiva of the eye of the patient, (xi) a change in the sticking value, representative of the average time of transitory residence of inflammatory cells to the blood vessels walls in the conjunctiva of the eye of the patient, (xii) a change in the average size of inflammatory cells in the lymph vessels in the conjunctiva of the eye of the patient, and/or (xiii) a change in the number of inflammatory cells present in the lymph vessels of the conjunctiva of the eye of the patient.

As noted, in some variations, determining the first blood flow characteristics and the second blood flow characteristics at the ocular surface of the eye of the patient may include performing at the first time instance and at the second time instance anterior segment (AS) optical coherence tomography angiography (OCTA) imaging for the ocular surface to detect blood flow at the ocular surface of the eye, and to produce images, based on the detected blood flow, representing a vasculature distribution at the ocular surface of the eye. Performing AS-OCTA for the ocular surface to detect blood flow at the ocular surface of the eye may include obtaining blood flow image data for multiple layers of the ocular surface, the multiple layers including one or more of, for example, cornea, limbus, conjunctiva, episcleral, and/or sclera. Obtaining the blood flow image data the multiple layers further may include dividing the image data for at least one of the multiple layers, based on a respective reference depth for the at least one of the multiple layers, into one or more of a superficial layer image data, deep layer image data, and/or full thickness image data. Embodiments of the therapeutic monitoring method may further include separating the blood flow image data into separate blood flow image data sets for one or more of the multiple layers.

Unless defined otherwise, all technical and scientific terms used herein have the same meaning as commonly or conventionally understood. As used herein, the articles "a" and "an" refer to one or to more than one (i.e., to at least one) of the grammatical object of the article. By way of example, "an element" means one element or more than one element. "About" and/or "approximately" as used herein when referring to a measurable value such as an amount, a temporal duration, and the like, encompasses variations of ±20% or ±10%, ±5%, or +0.1% from the specified value, as such variations are appropriate in the context of the systems, devices, circuits, methods, and other implementations described herein. "Substantially" as used herein when referring to a measurable value such as an amount, a temporal duration, a physical attribute (such as frequency), and the like, also encompasses variations of ±20% or ±10%, ±5%, or +0.1% from the specified value, as such variations are appropriate in the context of the systems, devices, circuits, methods, and other implementations described herein.

As used herein, including in the claims, "or" as used in a list of items prefaced by "at least one of" or "one or more of" indicates a disjunctive list such that, for example, a list of "at least one of A, B, or C" means A or B or C or AB or AC or BC or ABC (i.e., A and B and C), or combinations with more than one feature (e.g., AA, AAB, ABBC, etc.). Also, as used herein, unless otherwise stated, a statement that a function or operation is "based on" an item or condition means that the function or operation is based on the stated item or condition and may be based on one or more items and/or conditions in addition to the stated item or condition.

Although particular embodiments have been disclosed herein in detail, this has been done by way of example for purposes of illustration only and is not intended to be limiting with respect to the scope of the appended claims, which follow. Features of the disclosed embodiments can be combined, rearranged, etc., within the scope of the invention to produce more embodiments. Some other aspects, advantages, and modifications are considered to be within the scope of the claims provided below. The claims presented are representative of at least some of the embodiments and features disclosed herein. Other unclaimed embodiments and features are also contemplated.

What is claimed is:

1. A method comprising:
determining blood flow characteristics at an ocular surface of an eye of a patient, including
performing anterior segment (AS) optical coherence tomography angiography (OCTA) imaging for the ocular surface to detect blood flow at the ocular surface of the eye, obtaining blood flow image data for multiple layers of the ocular surface, the multiple layers comprise one or more of cornea, limbus conjunctiva, episcleral, and sclera;
determining characteristics of blood vessels at the ocular surface of the eye based on the blood flow characteristics, including
separating the blood flow image data into separate blood flow image data for one or more of the multiple layers, and
determining one or more of vessel density of the blood vessels at the ocular surface, diameters attributes of at least some of the blood vessels, and vasculature branching pattern attributes for the blood vessels measured by fractal dimension; and
deriving one or more ocular redness grading scales indicative of inflammation levels of the eye of the patient based on the characteristics of the blood vessels at the ocular surface of the eye.

2. The method of claim 1, wherein performing AS-OCTA for the ocular surface comprises:
producing images, based on the detected blood flow, representing a vasculature distribution at the ocular surface of the eye.

3. The method of claim 1, wherein obtaining the blood flow image data the multiple layers further comprises:
dividing the image data for at least one of the multiple layers, based on a respective reference depth for the at least one of the multiple layers, into one or more of a superficial layer image data, deep layer image data, or full thickness image data.

4. The method of claim 1, wherein separating the blood flow image data into separate blood flow image data sets for the respective multiple layers comprises:
separating the blood flow image data into the separate blood flow image data sets using machine learning techniques.

5. The method of claim 1, wherein performing AS-OCTA imaging for the ocular surface comprises:
controllably adjusting focus of a lens assembly of an OCT imaging apparatus based on one or more of: controllably actuating a focus-motor of the OCT imaging apparatus, or controllably actuating a z-motor of the OCT imaging apparatus to control a distance between the lens assembly and the eye of the patient.

6. The method of claim 1, wherein performing AS-OCTA imaging for the ocular surface comprises:
controlling an optical emission source of an OCT imaging apparatus to provide optical radiation controllably directed at the ocular surface, including performing one or more of: controllably adjusting the optical radiation directed to the eye of the patient so that light reflectance behavior is affected by tissue at the ocular surface of the eye, or controllably actuating activation and de-activation of the optical emission source provided to the OCT imaging apparatus.

7. The method of claim 1, wherein determining the characteristics of the blood vessels at the ocular surface comprises:
obtaining one or more images representative of a vasculature mapping at the ocular surface of the eye based on the determined blood flow characteristics; and
processing the one or more images to determine the characteristics of the blood vessels based on image data from the processed one or more images.

8. The method of claim 7, wherein processing the one or more images comprises:
identifying pixels, for a particular image from the one or more images, representing blood vessels in the image;
determining a ratio of the identified pixels representing the blood vessels in the image and total number of pixels in the particular image; and
determining the vessel density based on the determined ratio.

9. The method of claim 8, wherein identifying the pixels comprises:
binarizing the particular image to convert pixels value into either a pre-determined pixel value representing blood flow, or another pre-determine pixel value representing no blood flow.

10. The method of claim 7, wherein processing the one or more images comprises:
identifying pixels, for a particular image from the one or more images, representing non-vessel objects in the particular image;
generating a skeletonized image corresponding to the particular image comprising skeleton representations of blood vessels appearing in the particular image;
identifying skeletonized pixels, for the skeletonized image, representing non-vessel objects in the skeletonized image; and
deriving a vessel diameter index based on the identified pixels representing the non-vessel objects in the particular image and the identified skeletonized pixels representing the non-vessel objects in the skeletonized image.

11. The method of claim 7, wherein processing the one or more images comprises:
performing fractal dimension analysis of vessels appearing in the one or more images to determine vasculature branching pattern complexity of the blood vessels at the ocular surface of the eye.

12. The method of claim 1, further comprising:
determining one or more medical conditions of the patient based on the derived one or more ocular redness grading scales.

13. A system to determine inflammation level of an eye of a patient, the system comprising:

an imaging apparatus to determine blood flow characteristics at an ocular surface of the eye of the patient, comprising:

an anterior segment (AS) optical coherence tomography angiography (OCTA) imaging apparatus; and a controller configured to:

perform AS-OCTA imaging for the ocular surface to detect blood flow at the ocular surface of the eye;

determine characteristics of blood vessels at the ocular surface of the eye based on the determined blood flow characteristics;

determine one or more of vessel density of the blood vessels at the ocular surface, diameter attributes of at least some of the blood vessels, and vasculature branching pattern attributes for the blood vessels measured by fractal dimension; and derive one or more ocular redness grading scales indicative of inflammation levels of the eye of the patient based on the determined characteristics of the blood vessels at the ocular surface of the eye.

14. The system of claim 13, wherein the AS-OCTA imaging apparatus is configured to produce images based on the detected blood flow representing a vasculature distribution at the ocular surface of the eye.

15. The system of claim 13, wherein the controller configured to perform AS-OCTA imaging for the ocular surface to detect blood flow at the ocular surface is configured to:

obtain blood flow image data for multiple layers of the ocular surface, the multiple layers comprise one or more of: cornea, limbus, conjunctiva, episcleral, or sclera; and separate the blood flow image data into separate blood flow image data sets for:

one or more of respective multiple layers, or into one or more of a superficial layer, a deep layer, or full thickness layer.

16. The system of claim 15, wherein the controller further comprises a machine learning engine configured to separate the blood flow image data into the separate blood flow image data sets based on machine learning techniques.

17. The system of claim 13, wherein the controller configured to perform AS-OCTA imaging for the ocular surface is configured to:

controllably adjust focus of a lens assembly coupled to an OCT imaging apparatus based on one or more of: controllably actuating a focus-motor of the OCT imaging apparatus, or controllably actuating a z-motor of the OCT imaging apparatus to control a distance between the lens assembly and the eye of the patient.

18. The system of claim 13, wherein the controller to perform AS-OCTA for the ocular surface is configured to:

controllably actuate activation and de-activation of an optical emission source provided to the imaging apparatus.

19. The system of claim 13, wherein the controller configured to determine the characteristics of the blood vessels at the ocular surface is configured to:

obtain one or more images representative of a vasculature mapping at the ocular surface of the eye based on the determined blood flow characteristics; and process the one or more images to determine the characteristics of the blood vessels based on image data from the processed one or more images.

20. The system of claim 19, wherein the controller configured to process the one or more images is configured to:

identify pixels, for a particular image from the one or more images, representing blood vessels in the image;

determine a ratio of the identified pixels representing the blood vessels in the image and total number of pixels in the particular image; and determine the vessel density based on the determined ratio.

21. The system of claim 19, wherein the controller configured to process the one or more images is configured to:

identify pixels, for a particular image from the one or more images, representing non-vessel objects in the particular image;

generate a skeletonized image comprising skeleton representations of blood vessels appearing in the particular image;

identify skeletonized pixels, for the skeletonized image, representing non-vessel objects in the skeletonized image; and derive a vessel diameter index based on the identified pixels representing the non-vessel objects in the particular image and the identified skeletonized pixels representing the non-vessel objects in the skeletonized image.

22. The system of claim 19, wherein the controller configured to process the one or more images is configured to:

perform fractal dimension analysis of vessels appearing in the one or more images to determine vasculature branching pattern complexity of the blood vessels at the ocular surface of the eye.

23. Non-transitory computer readable media comprising computer instructions, executable on one or more processor-based devices, to:

determine blood flow characteristics at an ocular surface of an eye of a patient, including performing anterior segment (AS) optical coherence tomography angiography (OCTA) imaging for the ocular surface to detect blood flow at the ocular surface of the eye, obtaining blood flow image data for multiple layers of the ocular surface, the multiple layers comprise one or more of cornea, limbus, conjunctiva, episcleral, and sclera;

determine characteristics of blood vessels at the ocular surface of the eye based on the blood flow characteristics, including separating the blood flow image data into separate blood flow image data for one or more of the multiple layers, and determining one or more of vessel density of the blood vessels at the ocular surface, diameters attributes of at least some of the blood vessels, and vasculature branching pattern attributes for the blood vessels measured by fractal dimension; and derive one or more ocular redness grading scales indicative of inflammation levels of the eye of the patient based on the characteristics of the blood vessels at the ocular surface of the eye.

* * * * *